United States Patent
Zhou et al.

(10) Patent No.: US 11,897,955 B2
(45) Date of Patent: Feb. 13, 2024

(54) MONOCLONAL ANTIBODY BINDING TO TIGIT ANTIGEN, PREPARATION METHOD AND USE THEREOF

(71) Applicant: ACROIMMUNE BIOTECH CO., LTD., Guangzhou (CN)

(72) Inventors: Qunmin Zhou, Suzhou (CN); Weiwei Sun, Suzhou (CN); Zui Chen, Suzhou (CN); Xiaoxiao Ma, Suzhou (CN); Jinling Fan, Suzhou (CN); Hongqun Hu, Suzhou (CN)

(73) Assignee: ACROIMMUNE BIOTECH CO., LTD., Guangzhou (CN)

( * ) Notice: Subject to any disclaimer, the term of this patent is extended or adjusted under 35 U.S.C. 154(b) by 0 days.

(21) Appl. No.: 17/915,109

(22) PCT Filed: Jul. 15, 2020

(86) PCT No.: PCT/CN2020/102091
§ 371 (c)(1),
(2) Date: Mar. 20, 2023

(87) PCT Pub. No.: WO2021/217893
PCT Pub. Date: Nov. 4, 2021

(65) Prior Publication Data
US 2023/0272064 A1    Aug. 31, 2023

(30) Foreign Application Priority Data
Apr. 29, 2020    (CN) .......................... 202010353714.6

(51) Int. Cl.
| | | |
|---|---|---|
| C07K 16/02 | (2006.01) | |
| A61K 39/395 | (2006.01) | |
| A61P 35/00 | (2006.01) | |
| C07K 16/28 | (2006.01) | |
| C12N 15/85 | (2006.01) | |

(52) U.S. Cl.
CPC .............. *C07K 16/28* (2013.01); *A61P 35/00* (2018.01); *C07K 16/2818* (2013.01); *C07K 16/2827* (2013.01); *C12N 15/85* (2013.01); *C07K 2317/76* (2013.01); *C12N 2800/107* (2013.01)

(58) Field of Classification Search
None
See application file for complete search history.

(56) References Cited

U.S. PATENT DOCUMENTS

| | | |
|---|---|---|
| 9,499,596 B2 | 11/2016 | Clark et al. |
| 9,713,641 B2 | 7/2017 | Hicklin et al. |
| 10,017,572 B2 | 7/2018 | Grogan et al. |
| 10,189,902 B2 | 1/2019 | Maurer et al. |
| 10,544,219 B2 | 1/2020 | Gurney et al. |
| 10,618,958 B2 | 4/2020 | Williams et al. |

FOREIGN PATENT DOCUMENTS

| | | |
|---|---|---|
| CN | 109384846 A | 2/2019 |
| CN | 109734806 A | 5/2019 |
| CN | 110997720 A | 4/2020 |
| CN | 111050788 A | 4/2020 |
| WO | 2016028656 A1 | 2/2016 |
| WO | 2016106302 A1 | 6/2016 |

OTHER PUBLICATIONS

Zeng et al. (2021) Journal of Experimental & Clinical Cancer Research 40:285, p. 1-11.*
Xin Yu, et al., The surface protein TIGIT suppresses T cell activation by promoting the generation of mature immunoregulatory dendritic cells, Nature Immunology, 2009, pp. 48-57, vol. 10 No. 1.
Kent S. Boles, et al., A novel molecular interaction for the adhesion of follicular CD4 T cells to follicular dendritic cells, Eur J Immunol., 2009, pp. 1-13, 39(3).
Steven D. Levin, et al., Vstm3 is a Member of the CD28 Family and an Important Modulator of T Cell Function, Eur J Immunol., 2011, pp. 1-22, 41(4).
Noa Stanietsky, et al., The interaction of TIGIT with PVR and PVRL2 inhibits human NK cell cytotoxicity, 2009, pp. 17858-17863, vol. 106 No. 42.
Ying Wang, et al., Degenerated primer design to amplify the heavy chain variable region from immunoglobulin cDNA, BMC Bioinformatics, 2006, pp. 1-7, 7(Suppl 4): S9.
G. Kohler, et al., Continuous cultures of fused cells secreting antibody of predefined specificity, Nature, 1975, pp. 495-497, vol. 256.

* cited by examiner

*Primary Examiner* — Ilia I Ouspenski
(74) *Attorney, Agent, or Firm* — Bayramoglu Law Offices LLC

(57) ABSTRACT

A monoclonal antibody or a derivative thereof that binds to a human TIGIT antigen with high-affinity and antagonistically inhibits the binding of TIGIT to a ligand thereof such as CD155 is provided. Amino acid sequences of antigen complementarity-determining regions CDR-L1, CDR-L2 and CDR-L3 of an antibody light chain variable region, and amino acid sequences of antigen complementarity-determining regions CDR-H1, CDR-H2 and CDR-H3 of an antibody heavy chain variable region are specified. Further, a humanization preparation method for the antibody and amino acid sequences of the heavy chain variable region and light chain variable region of the humanized antibody are provided. The antibody or the derivative thereof can serve as an ingredient of a pharmaceutical composition or can be prepared into an appropriate drug preparation, and administered alone or in combination with other medications, such as an anti-PD-1 monoclonal antibody, or treatment means, for treating diseases such as tumors.

20 Claims, 10 Drawing Sheets
Specification includes a Sequence Listing.

Sequence alignment of human TIGIT and mouse TIGIT

*Signal peptide* hTIGIT 1    MRWCLLLIWAQGLRQAP-LASGM MTGTIETTGNISAEKGGSIILQCHLSSTTAQVTQVNW
59

M   LLL+W QGL QA   LA+G    GTI+T  NISAE+GGS+ILQCH SS TA+VTQV+W mTIGIT 1    MHGWLLLVWVQGLIQAAFLATGA TAGTIDTKRNISAEEGGSVILQCHFSSDTAEVTQVDW
60 hTIGIT 60   EQQDQLLAICNADLGWHISPSFKDRVAPGPGLGLTLQSLTVNDTGEYFCYHTYPDGTYT
119

+QQDQLLAI + DLGWH++    F DRV PGP LGLT QSLT+NDTGEYFC YHTYP G Y mTIGIT 61   KQQDQLLAIYSVDLGWHVASVFSDRVVPGPSLGLTFQSLTMNDTGEYFCTYHTYPGGIYK
120

Transmembrane domain hTIGIT 120  GRIFLEVLESSVAEHGARFQI-PLLGAMAATLVVICTAVIVVVALT RKKKALRIHSVEGD
178

GRIFL+V ESSVA+     FQ  PL G MAA L +IC  V  V   L R KK+++R+HS+E mTIGIT 121  GRIFLKVQESSVAQ----FQTAPLGGTMAAVLGLICLMVTGVTVLA R-KKSIRMHSIESG
175 hTIGIT 179  LRRKSAGQEEWSPSAPSPPGSCVQAEAAPAGLCGEQRGEDCAELHDYFNVLSYRSLGNCS
238

L R  A  +EW+  +   S PGS VQ + APAG CGEQ    +D A+   +YFNVLSYRSL + mTIGIT 176  LGRTEAEPQEWNLRSLSSPGSPVQTQTAPAGPCGEQAEDDYADPQEYFNVLSYRSLESFI
235 hTIGIT 239  FFTETG  244
                   ++TG
mTIGIT 236  AVSKTG  241

FIG. 1

MONOCLONAL ANTIBODY BINDING TO TIGIT ANTIGEN, PREPARATION METHOD AND USE THEREOF

CROSS REFERENCE TO THE RELATED APPLICATIONS

This application is the national phase entry of International Application No. PCT/CN2020/102091, filed on Jul. 15, 2020, which is based upon and claims priority to Chinese Patent Application No. 202010353714.6, filed on Apr. 29, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHHY018-sequence listing-20220708.txt, created on 07/19/2022, and is 8,780 bytes in size.

TECHNICAL FIELD

The present invention belongs to the field of biotechnology-antibody. The present invention relates to an antibody antagonistically inhibiting the binding of TIGIT (T-cell immunoreceptor with Ig and ITIM domain protein) to its ligand, coding sequences thereof, as well as preparation method and use thereof.

BACKGROUND

T lymphocyte-mediated cellular immunity plays a key role in recognizing, monitoring, attacking, and killing tumor cells. T lymphocytes mediate their immune response via the interaction of so-called co-stimulatory molecules or co-inhibitory molecules to their corresponding ligands, which are expressed in their targeting tumor cells or antigen-presenting cells (APC). Co-inhibitory factors are also known as immune checkpoint inhibitory molecules, which include CTLA-4 (Cytotoxic T-lymphocyte Antigen-4) and its ligands B7-1 (CD80) and B7-2 (CD86); programmed death receptor (PD-1), and its ligands PD-L1 and PD-L2; lymphocyte activation gene-3 (LAG-3) and its ligand; TIM-3 (T-cell immunoglobulin domain and mucin domain 3) and its ligands; BTLA (B and T lymphocyte attenuator) and its ligands, etc. These immune checkpoint molecules are similar in structure and most of them belong to the immunoglobulin superfamily.

There have been a number of monoclonal antibody (mAb) type drugs antagonistically inhibiting CTLA-4 or PD-1/PD-L1 approved and being on the market, and these mAb drugs have been shown to have significant treatment efficacy for a variety of tumors. For example, Ipilimumab (YERVOY), an anti-CTLA-4 monoclonal antibody was approved by the U.S. Food and Drug Administration (FDA) in 2011 for the treatment of the advanced Melanoma; Nivolumab (Opdivo) and Pembrolizumab (Keytruda), two anti-PD-1 mAbs, were approved in 2014 for the treatment of Non-Small Cell Lung Cancer (NSCLC); and Atezolizumab (Tecentriq), an anti-PD-L1 mAb, was approved in 2016 for the treatment of Non-Small Cell Lung Cancer.

Currently, one of the hot topics in the immunotherapy field is to identify new targets for developing mAb-based drugs like those mAbs targeting the inhibitory immune checkpoint molecules such as CTLA-4 and PD-1/PD-L. TIGIT appears to be one of these newly discovered inhibitory immune checkpoint molecules with a similar potential for developing new drugs.

TIGIT (T cell immunoreceptor with Ig and ITIM domain) was first discovered and reported by Yu X, et al. in 2009 (Yu X: Nat Immunol. 2009, 10:48-57). TIGIT is also known as WUCAM (Washington University cell adhesion molecule) (Vermi K S: Eur J Immunol 2009, 39:695-703), VSTM3 (V-set and transmembrane domain-containing protein 3, Levin S: Eur J Immunol 2011, 41:902-915) or VSIG9 (V-set and immunoglobulin domain-containing protein 9).

The full length human TIGIT protein contains 244 amino acids, including 141 in the extracellular region, 23 in the transmembrane region, and 80 in the cytoplasmic region. The full length mouse TIGIT protein contains 241 amino acids, with a 60% sequence homology to human TIGIT protein. One important structural feature of TIGIT protein is that its intracellular region contains a typical immunoreceptor tyrosine-based inhibition motif (ITIM), which can mediate immune-suppression signals. ITIM also exists in the intracellular region of the PD-1 molecule.

Similar to PD-1, TIGIT is mainly expressed by T cells (including helper T cells, memory T cells, and CD8+ effector T cells) and natural killer (NK) cells, whereas its ligands are mainly expressed in antigen-presenting cells such as dendritic cells (DC) and macrophages, as well as tumor cells or other T-cell targeting cells.

There are three known ligands that recognize and bind to TIGIT, namely CD155, CD112, and CD113. CD155 is also known as the poliovirus receptor (PVR); CD112 and CD113 are also known as poliovirus receptor-related protein-2 (PVRL-2) and poliovirus receptor-related protein-3 (PVRL-3), respectively. CD155 binds to TIGIT more strongly than CD112 or CD113 dose (Yu X, Nat Immunol. 2009, 10:48-57; Stanietsky N, Proc Natl Acad Sci USA. 2009, 106: 17858-63). CD155, CD112 and CD113 are all members of the Nectin family.

CD155 or CD112 can also bind to the co-stimulatory molecule CD226 (DNAM-1) and generates or up-regulates T cell response. However, CD155 or CD112 binds more strongly to the inhibitory immune molecule TIGIT than to CD226 (DNAM-1). This dynamic interaction system formed by TIGIT-CD226/CD155-CD112 interaction is similar to those seen in the CD28-CTLA4/CD80-CD86 immune interaction system.

CD155 is expressed at a relatively low level in normal human cells and at a high level in many tumor cells. By up-regulating CD155 expression, tumor cells can inhibit the immune attacking or killing by the host T cells/NK cells. Therefore, with the development of mAbs that can antagonistically inhibit the binding of TIGIT to its ligand such as CD155, the immune-suppression can be relieved and the immune attacking or killing of tumor cells by the host T cells/NK cells can be restored.

Currently, there is no any TIGIT targeting drug that has been approved or on the market, but many pharmaceutical companies, such as Genentech, Bristol-Myers Squibb (BMS), MSD, and OncoMed, have developed their anti-TIGIT antibody drugs and filed relevant patent application/protection. The anti-TIGIT mAb Tiragolumab (code-name: MTIG-7192A) from Genentech Inc. has been in the leading development stage. Tiragolumab has entered into the phase III clinical trial study in combination with the anti-PD-L1 mAb Atezolizumab (trade name Tecentriq, Genentech) for the treatment of Non-Small Cell Lung Cancer. Genentech has filed a series of patent applications for its anti-TIGIT monoclonal antibodies, and two patents have been granted by the USPTO (U.S. Pat. Nos. 9,499,596B2 and 10,017,572B2).

The BMS's anti-TIGIT monoclonal antibody (Codename: MBS-986207), either use alone or in combination with BMS's anti-PD-1 drug Nivolumab (Opdivo), is currently in a phase II clinical trial study. BMS has filed patents for its anti-TIGIT mAbs and granted by the USPTO (US Patent Application No. 2016/0176963 A1; and granted U.S. Pat. No. 10,189,902B2).

The MSD's anti-TIGIT monoclonal antibody (codenamed MK-7684), is in Phase I/II clinical study for the combination use with Pembrolizumab (Keytruda) for the treatment of tumors. MSD has filed patent applications for its anti-TIGIT monoclonal antibody and was granted a patent by the USPTO (US Patent Application No. 2016/0355589 A1; granted U.S. Pat. No. 10,618,958B2).

In addition, several other anti-TIGIT monoclonal antibodies developed by other overseas companies have also moved into the clinical study stage. These mAbs include mAb ASP8374 (granted U.S. Pat. No. 9,713,641B2) from Potenza Therapeutics company; mAb OMP-313M32 (US Patent Application No. 2016/0376365 A1; U.S. Pat. No. 10,544,219B2) from OncoMed, mAb AB-154 from Arcus Biosciences.

Since the mouse TIGIT protein and the human TIGIT protein have only approximately 60% homology in the amino acid sequence, therefore, in theory, novel monoclonal antibodies targeting different epitopes of TIGIT antigen can be produced or developed by using traditional protein antigen immunization in mice and hybridoma production technique. These novel mAbs can be used as a single agent or in combination with other mAb-based medicines being developed or on the market such as anti-PD-1 mAb, anti-CTLA-4 mAb, anti-41BB mAb, anti-OX40 mAb, anti-CD38 mAb, anti-CD47 mAb, anti-VISTA mAb, anti-BTLA mAb, anti-VEGF/VEGFR mAb for the treatment of a variety of diseases including tumors.

One of the aims of the present invention is to obtain novel mAbs that can bind to human TIGIT antigen with high-affinity and antagonistically inhibit the binding of TIGIT antigen to its ligands such as CD155 (PVR) or CD112 (PVRL-2). These antibodies, or their derivatives, can be used as pharmaceutical ingredients either alone or in combination with other medicines that have been already on the market or in the development stage to treat a variety of diseases including tumors.

SUMMARY

A technical issue to be solved in the present invention is to provide an antibody or a derivative thereof such as an antibody Fab fragment, a single-chain antibody, etc. The antibody or the derivative thereof can bind to human TIGIT antigen with high-affinity and antagonistically inhibit the binding of TIGIT antigen to its ligands such as CD155 (PVR).

A second technical issue to be solved in the present invention is to provide a DNA molecule or gene sequence encoding the above antibody.

A third technical issue to be solved in the present invention is to provide a pharmaceutical compound or a pharmaceutical composition comprising the above antibody or its derivatives.

A fourth technical issue to be solved in the present invention is to provide a use of the above antibody or derivative thereof for the preparation of a medicament for the treatment of tumors.

A fifth technical issue to be solved is to provide a preparation method for the above antibody or derivative thereof.

To resolve the above technical issues, the present invention adopts the following technical solutions:

In one aspect, the present invention provides an antibody or a derivative thereof binding to human TIGIT antigen with high-affinity and antagonistically inhibiting the binding of TIGIT antigen to its ligand CD155, comprising a first variable region and a second variable region, wherein the first variable region is an antibody light chain variable region comprising complementarity-determining regions CDR1, CDR2, and CDR3 having amino acid sequences as set forth in SEQ ID NO: 9, SEQ ID NO: 10 and SEQ ID NO: 11, respectively; and wherein the second variable region is an antibody heavy chain variable region comprising complementarity-determining regions CDR1, CDR2, and CDR3 having amino acid sequences as set forth in SEQ ID NO: 14, SEQ ID NO: 15 and SEQ ID NO: 16, respectively.

The antibody comprises a humanized monoclonal antibody, and the derivative thereof comprises an antibody Fab fragment, a single-chain antibody, a bi-specific antibody, etc.

As a preferred technical solution, the antibody or derivative thereof has one or more of the following characteristics:
d) comprising an antibody light chain variable region and antibody heavy chain variable region, the amino acid sequence of the antibody light chain variable region is at least 90% identical to the amino acid sequence shown in SEQ ID NO: 17; and the amino acid sequence of the antibody heavy chain variable region is at least 90% identical to the amino acid sequence shown in SEQ ID NO: 19;
e) its KD value of the binding-affinity with human TIGIT antigen is equal to or less than 10 nM, the KD value can be determined by Fortebio-Octet, BIACORE, or other similar surface plasmon resonance (SPR) techniques;
f) antagonistically inhibiting the binding of TIGIT to its ligands, CD155 (PVR) or CD112 (PVRL-2). As a preferred technical solution, the half-maximal inhibitory concentration ($IC_{50}$) of inhibiting the binding of TIGIT to CD155 (PVR) is equal to or less than 1 nM ($IC_{50}$ refers to the concentration at which a substance is at half its maximum inhibitory effect)

As a preferred technical solution, the first variable region is an antibody light chain variable region having an amino acid sequence as set forth in SEQ ID NO: 17; and the second variable region is an antibody heavy chain variable region having an amino acid sequence as set forth in SEQ ID NO: 19.

As a preferred technical solution, the first variable region is an antibody light chain variable region having an amino acid sequence as set forth in SEQ ID NO: 8; and the second variable region is an antibody heavy chain variable region having an amino acid sequence as set forth in SEQ ID NO: 13.

As a preferred technical solution, the antibody or the derivative thereof antagonistically inhibits the binding of TIGIT to its ligands, CD155 (PVR) or CD112 (PVRL-2).

As a preferred technical solution, the monoclonal antibody or the derivative comprises the antibody light chain variable region, a human antibody light chain constant region, the antibody heavy chain variable region, and a hinge region of a human antibody heavy chain constant region, CH1 region, CH2 region, and CH3 region.

As a preferred technical solution, wherein the human antibody light chain constant region is a kappa chain or a lambda chain of the human antibody, and the human antibody heavy chain constant region is a human IgG1, IgG2, IgG3, or IgG4 isotype, wherein the IgG4 isotype is more preferred.

In a second aspect, the present invention provides a DNA molecule or gene sequence (corresponding to the following antibody or derivative thereof: the first variable region is an antibody light chain variable region having an amino acid sequence as set forth in SEQ ID NO: 17; and the second variable region is an antibody heavy chain variable region having an amino acid sequence as set forth in SEQ ID NO: 19) coding the above antibody or derivative thereof, a nucleotide sequence coding the antibody light chain variable region as set forth in SEQ ID NO: 18, and a nucleotide sequence coding the antibody heavy chain variable region as set forth in SEQ ID NO: 20.

The present invention also provides a DNA molecule or gene sequence (corresponding to the following antibody or derivative thereof: the first variable region is an antibody light chain variable region having an amino acid sequence as set forth in SEQ ID NO: 8; and the second variable region is an antibody heavy chain variable region having an amino acid sequence as set forth in SEQ ID NO: 13) coding the above antibody or the derivative thereof, a nucleotide sequence coding the antibody light chain variable region as set forth in SEQ ID NO: 7, and a nucleotide sequence of the antibody heavy chain variable region as set forth in SEQ ID NO: 12.

In a third aspect, the present invention provides an expression vector comprising a DNA molecule or gene sequence coding the above antibody or the derivative thereof and an expression regulatory sequence operably linked to the DNA molecule or gene.

In a fourth aspect, the present invention provides a recombinant host cell transfected with the above expression vector. The recombinant host cell or its progeny cells expresses the above antibody or derivative thereof. The antibody comprises a humanized monoclonal antibody, and the derivative thereof comprises an antibody Fab fragment, a single-chain antibody, a bi-specific antibody, etc.

In a fifth aspect, the present invention provides a pharmaceutical compound or a pharmaceutical composition, comprising a pharmaceutically valid amount of the antibody or the derivative thereof and a pharmaceutically accepted carrier. The pharmaceutical composition comprises other similar antibodies such as anti-PD-1 antibodies or anti-PDL-1 antibodies and medications.

In a sixth aspect, the present invention provides a use of the antibody or derivative thereof for the preparation of a medicament for the treatment of tumors. The antibody can be used as a single agent or in combination with other medications that are being in the development stage or on the market such as anti-PD-1 mAb, anti-PDL1 mAb, anti-CTLA-4 mAb, anti-41BB mAb, anti-OX40 mAb, anti-CD2 mAb, anti-CD3 mAb, anti-CD20 mAb, anti-CD24 mAb, anti-CD27 mAb, anti-CD28 mAb, anti-CD33 mAb, anti-CD38 mAb, anti-CD40 mAb, anti-CD47 mAb, anti-BTLA mAb, anti-EGFR mAb, anti-Her2 mAb, anti-VISTA mAb, anti-VEGF mAb, and anti-VEGFR mAb, to treat a variety of diseases including tumors.

In specific examples of the invention, the invention describes the application of anti-TIGIT monoclonal antibody 33D2 and anti-PD-1 monoclonal antibody to inhibit the growth of colon cancer in mice.

In a seventh aspect, the present invention provides a method for preparing the antibody or the derivative thereof, wherein the method comprises the following steps:
  e) providing the above expression vector, the expression vector comprises the above DNA molecule or gene coding the antibody or the derivative thereof and an expression regulatory sequence operably linked to the DNA molecule or gene;
  f) transfecting a host cell with the expression vector of step a);
  g) culturing the host cell from step b) under conditions suitable for the expression of the antibody; and
  h) isolating, purifying, and collecting the antibody or derivative from the host cell culture medium by affinity chromatography.

The term "monoclonal antibody (mAb)" used herein refers to an immunoglobin obtained from a clonal cell, with the same structure and chemical characteristics and specific to a single antigenic determinant. The monoclonal antibody is different from a regular polyclonal antibody preparation (usually having different antibodies directed against different determinants) and each monoclonal antibody is directed against a single determinant of an antigen. In addition to its specificity, the monoclonal antibody is also advantageous because it is cultured from hybridoma or recombinant engineering cells and will not be mixed with other immunoglobulins. The modifier "monoclonal" indicates that the antibody's properties are achieved from a homogeneous population of antibodies, which should not be interpreted as any special method that needs to be used for the manufacturing of antibodies.

The term "humanized monoclonal antibody" as used herein refers to that all or most of the amino acid sequences of the murine monoclonal antibodies (including the framework region sequence in the variable region), except complementarity-determining regions (CDR) are substituted by the amino acid sequences of human immunoglobulins, to reduce the immunogenicity of the murine monoclonal antibody to the utmost extent by genetic engineering methods.

The terms "antibody" and "immunoglobulin" used herein refer to an iso-tetra proteoglycan of about 150,000 Daltons with the same structural characteristics and consist of two identical light chains (L) and two identical heavy chains (H). Each light chain is linked to the heavy chain through a covalent disulfide bond, while the same isotype heavy chains of the different immunoglobulins have a different amount of disulfide bonds. Each heavy chain and each light chain also have regularly spaced intrachain disulfide bonds. Each heavy chain has a variable region ($V_H$) at one end, followed by several constant regions. Each light chain has a variable region ($V_L$) at one end, and a constant region at the other end. The constant region of the light chain is opposite to the first constant region of the heavy chain. The variable region of the light chain is opposite to the variable region of the heavy chain. Special amino acid residues form an interface between the variable region of the light chain and the heavy chain.

The term "variable" used herein indicates that some portions of the variable region in an antibody are different in sequence, which results in the binding and specificity of various specific antibodies to the specific antigens. However, variability is not evenly distributed throughout the whole antibody variable region. Instead, it concentrates on three fragments in the complementarity-determining region (CDR) and hypervariable region in the light-chain or heavy-chain variable regions. The definition of the amino acid sequence of complementary determination region (CDR) can refer to the Kabat system (Kabat, E. A., et al. (1991) Sequences of Proteins of Immunological Interest, Fifth Edition, U.S. Department of Health and Human Services, NIH Publication No. 91-3242) or see Table 1).

In the description of the invention, the Kabat system is used to define the amino acid sequence of the complementary determination region (CDR).

TABLE 1

Residues in CDR according to Kabat, Chothia numbering, or based on crystal structure (contact) Definition of amino acid sequences of complementary determination region (CDR)

| | | | |
|---|---|---|---|
| L1 | L24-L34 | L26-L32 | L30-L36 |
| L2 | L50-L56 | L50-L56 | L46-L55 |
| L3 | L89-L97 | L89-L97 | L89-L96 |
| H1 | H31-H35B | H26-H32 | H30-H35B |
| | (Kabat Numbering) | | |
| H1 | H31-H35 | H26-H32 | H30-H35 |
| | (Clothia Numbering) | | |
| H2 | H50-H65 | H53-H55 | H47-H58 |
| H3 | H95-H102 | H96-H101 | H93-H101 |

The more conservative part of the variable region is called the framework region (FR). There are four FR regions in each variable region of the heavy-chain and light-chain of an antibody. The FR regions are roughly in a β-folded configuration and connected by three CDRs forming a connecting loop. The partial β-folded configuration can form in some cases. The CDRs in each chain are close together through the FR regions and form the antigen-binding site of the antibody together with the CDRs of another chain (see Kabat et al, NIH Publ. No. 91-3242, Vol. 1, pp. 647-669 (1991)). The antibody's constant region does not directly participate in the binding of the antibody to the antigen. Still, it exhibits different effects and functions, such as participating in antibody-dependent cellular cytotoxicity (ADCC) and complement-dependent cytotoxicity (CDC) of the antibody.

The antibody of the present invention can be usually prepared by the following methods:

Firstly, insert the gene coding the antibody in the present invention into the expression vector containing a suitable expression regulatory sequence. The term "expression regulatory sequence" used herein usually refers to a sequence that participates in the control of the gene expression. The expression regulatory sequence includes a promoter operable linked to the target gene and a termination signal. The gene (DNA) sequence of the present invention's antibody can be encoded by the common techniques well known by the skilled in the art, such as artificial synthesis according to the protein sequences disclosed by the present invention or the PCR amplification. After that, the DNA fragments synthesized or amplified by the PCR method can be inserted into a suitable expression vector by various methods well known in the art.

The expression vector used in the present invention can be available on the market and well known to those skilled in the art, such as the pCDNA3.1 expression vector from Invitrogen or self-made vectors such as pQY series vectors from own company.

The suitable host cells for accepting the expression vector transformation generally include both prokaryotes and eukaryotes. Commonly used prokaryotes host cells include *E. coli, Bacillus subtillis*, etc. Commonly used eukaryotes host cells include yeast cells, insect cells, and mammalian cells. In the present invention, the preferred host cells are mammalian, particularly Chinese hamster ovary (CHO) cells such as CHO-S.

The host cells transfected by the expression vector are cultured under suitable conditions (e.g., culturing with serum-free culture medium in a cell culture flask or bioreactor by adhesion to the wall or suspension). The supernatant is collected and purified by common separation steps or means well known by the skilled in the art, including protein-A affinity chromatography, ion-exchange chromatography, filtration, etc. to produce the antibodies of the present invention. The purified antibodies of the present invention can be dissolved in an appropriate solvent such as sterile saline liquid. The solubility can be prepared between 0.01 and 100 mg/mL. The ideal final solubility can be prepared between 1 mg/ml and 20 mg/ml.

The antibodies or derivatives thereof can be used as pharmaceutical ingredients alone or in combination with other medications that are being in the development stage or on the market such as anti-PD-1 mAb, anti-PDL1 mAb, anti-CTLA-4 mAb, anti-41BB mAb, anti-OX40 mAb, anti-CD2 mAb, anti-CD3 mAb, anti-CD20 mAb, anti-CD24 mAb, anti-CD27 mAb, anti-CD28 mAb, anti-CD33 mAb, anti-CD38 mAb, anti-CD40 mAb, anti-CD47 mAb, anti-BTLA mAb, anti-EGFR mAb, anti-Her2 mAb, anti-VISTA mAb, anti-VEGF mAb, and anti-VEGFR mAb, to treat a variety of diseases including tumors.

In particular, the invention describes a combined administration of the antibody or its derivative with anti-PD-1 monoclonal antibodies, which was used to test its activity in vivo in the TIGIT/PD-1 double humanized mice (human PD-1 and human TIGIT double gene knock-in mice) (see Example 10). The test results show that the anti-TIGIT antibody in the present invention, either given alone or combined with anti-PD-1 monoclonal antibodies, shows obvious anti-tumor efficacy.

In order to obtain hybridoma cell lines secreting murine monoclonal antibodies that can bind to human TIGIT antigen with high-affinity and antagonistically inhibit the binding of TIGIT to its ligand CD155, the present invention selected a recombinant human TIGIT extracellular protein expressed by mammals as an immune antigen, through repeated low-dose subcutaneous immunization to mice. Polyclonal antibodies were obtained from mice and used for screening mouse sera with anti-TIGIT activities; then, the mice with high titer antibodies were selected and their spleen cells were isolated and fused with mouse myeloma cells in vitro. After drug screening and sub-cloning, a number of monoclonal hybridomas stably secreting antibodies against human TIGIT antigen were obtained. One murine hybridoma subclone, m33D2 (33D2 for short), identified by ELISA, western blot, immunohistochemistry, and in vitro competitive binding assay with TIGIT ligand was shown that it not only binds to human TIGIT protein with a high-affinity but also antagonistically inhibits the binding of TIGIT protein to its ligands (such as CD155 and CD112).

The present invention obtained the gene fragments encoding the heavy chain variable region and light chain variable region of the murine antibody through genetic engineering, and on this basis carried out human-mouse chimeric and humanized genetic engineering transformation of the antibody. The gene encoding human-mouse chimeric antibody (c33D2) or humanized antibody (h33D2) was transfected into Chinese hamster ovary (CHO) cells to produce recombinant cells stably secreting and expressing chimeric antibody or humanized antibody, further human-mouse chimeric and humanized antibodies with bioactivity antagonizing TIGIT are isolated and purified and obtained from a recombinant engineering cell culture medium.

This anti-TIGIT antibody can be used as a single agent or in combination with other medications that are being in the development stage or on the market such as anti-PD-1 mAb, anti-PDL1 mAb, anti-CTLA-4 mAb, anti-41BB mAb, anti-OX40 mAb, anti-CD2 mAb, anti-CD3 mAb, anti-CD20 mAb, anti-CD24 mAb, anti-CD27 mAb, anti-CD28 mAb, anti-CD33 mAb, anti-CD38 mAb, anti-CD40 mAb, anti-CD47 mAb, anti-BTLA mAb, anti-EGFR mAb, anti-Her2 mAb, anti-VISTA mAb, anti-VEGF mAb, and anti-VEGFR mAb, to treat a variety of diseases including tumors.

BRIEF DESCRIPTION OF THE DRAWINGS

FIG. 1 is a schematic diagram of amino acid sequence comparison analysis of human TIGIT protein and mouse TIGIT protein, as in Example 1 of the present invention.

DETAILED DESCRIPTION OF THE EMBODIMENTS

Figure 2:
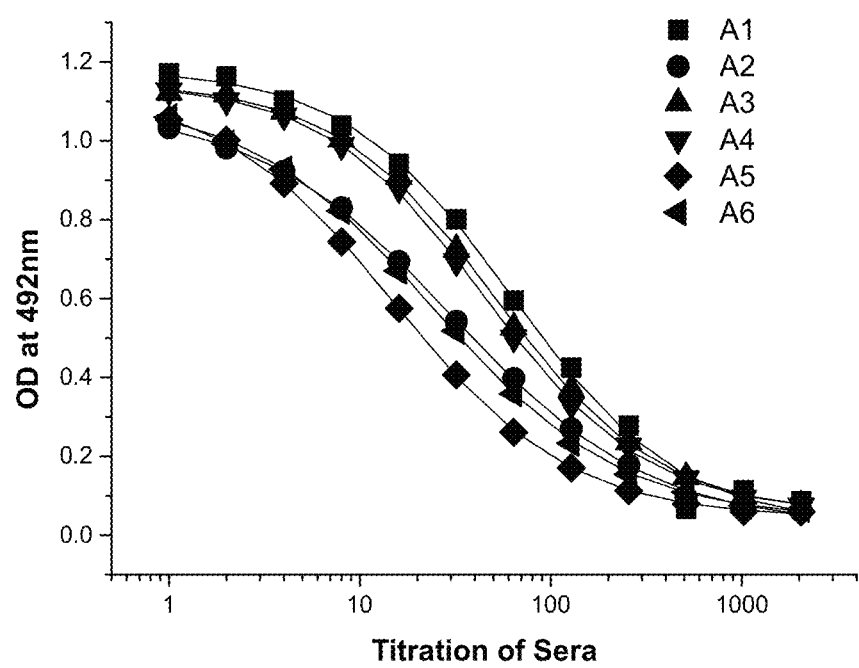
FIG. 2 is a schematic diagram showing the anti-TIGIT antibody titer detected in sera from immunized mice, as in Example 1 of the present invention. The detected method is an ELISA using a 96-well plate coated with recombinant human TIGIT extracellular protein.

The present invention will be further described by reference to the following examples, which are illustrative only and are not intended to limit the present invention.

Example 1. Production and Screening of Mouse Hybridoma Cell Lines that Secrete Anti-TIGIT Antibody 3) Comparison Analysis of the Amino Acid Sequence of Human TIGIT Protein and Mouse TIGIT Protein A comparison analysis result of the amino acid sequence of human TIGIT protein and mouse TIGIT protein was shown in FIG. 1, wherein the amino acid sequence marked in italics in the box is the signal peptide that leads the exocytic expression of TIGIT protein, and the amino acid sequence marked in bold with underline in the box is the transmembrane domain of TIGIT protein. As shown in FIG. 1, there is only 60% homology in the amino acid sequence between human TIGIT protein and mouse TIGIT protein. In their extracellular region which is directly involved in the recognition and binding to its ligands (CD155 or CD112), there are more than 30 different amino acid sequence or sites between human TIGIT and mouse TIGIT proteins. Therefore, it is speculated that mouse anti-human TIGIT monoclonal antibodies can be generated by using a traditional protein antigen immunization in mouse coupled with hybridoma preparation techniques.

4) Generation and Screening of Mouse Hybridoma Cell Lines that Secrete Anti-TIGIT Antibody Step 1: Source of Recombinant Human TIGIT Protein (Immunizing Antigen) and Animals Used for Immunization In the example of the present invention, the immunizing antigen is a recombinant human TIGIT extracellular membrane protein with a C-terminal histidine tag expressed by mammalian cells (TIGIT-His, Sino Biological Inc. Product No. 10818-H08H). The recombinant human TIGIT-His protein was mixed with Complete Freund's Adjuvant (Sigma, USA) and injected into Balb/c mice subcutaneously at multi-points (100 μl/mouse, 10 μg TIGIT-His protein each time). Two to three weeks after the first immunization, TIGIT-His protein was mixed with Incomplete Freund's Adjuvant (Sigma, USA) and subcutaneously immunized mice at multi-points; after the mice were boosted three to four times, a small amount of serum was collected from the mice, then the anti-TIGIT antibody titers in mouse serum were detected by ELISA method using a 96-well plate coated with the recombinant human TIGIT-His protein, spleen cells with from mice with high serum titer were used for further cell fusion.

Step 2: Cell Fusion

Three to four days after the last immunization, the mouse splenocyte cell suspensions were prepared in a sterile condition, then fused with mouse SP2/0 myeloma cells (purchased from Cell Center of Shanghai Institute of Life Sciences, Chinese Academy of Sciences) at a ratio of 5:1 or 10:1 at 50% PEG-1000 (Sigma, USA) based upon standard protocols (Kohler G and Milstein C: Nature 1975; 256:495-497), about 1 mL PEG was added slowly within 60 seconds, let the fusion reacted for 90 seconds, and then the reaction was terminated by adding serum-free RPMI-1640 culture medium, centrifuged 10 minutes with 1000 rpm to remove the supernatant; after the centrifugation, the precipitated cells were collected and the cell density was adjusted to $1 \times 10^6$/ml with RPMI 1640-10% FCS culture medium containing 10% HAT (H for hypoxanthine, A for aminopterin, T for thymidine nucleoside) (Sigma, USA), then added into 96-well flat-bottom cell culture plates (200 ul/well), and incubated in an incubator (Thermo, USA) containing 5% $CO_2$ at 37° C. for two to three weeks.

Step 3: Screening of Mouse Hybridoma Cell Lines Secreting Anti-TIGIT Antibody by ELISA Similarly, 96-well plates were coated with the recombinant human TIGIT-his protein (2 μg/ml, pH 9.6, 0.1 M $NaHCO_3$ solution) at 37° C. for 2 hours, 2% Bovine Serum Albumin (BSA) was added and sealed overnight at 4° C. The next day, the coated plates were washed with PBS-0.1% Tween20 solution, followed by an addition of the hybridoma cell culture supernatants to be detected (an unfused SP2/0 myeloma cell culture supernatant as a negative control) and incubated at 37° C. for 2 hours; after washing with PBS-0.1% Tween20 solution, an HRP-labeled Goat anti-Mouse IgG antibody (Sigma, USA) was added and incubated at 37° C. for 1 hour; after washing with PBS-0.1% Tween20 solution again, a substrate solution o-Phenylenediamine (OPD)-0.1% $H_2O_2$ was added for a color development for about 10-15 minutes, then 0.1M HCl solution was added to quench the reaction. Thereafter, the OD values at 492 nm were read in an MK3-Multiskan microplate reader. The supernatant samples from hybridoma cells with OD 492 values at 5-10 fold higher than that of the negative control sample were re-tested, and these hybridoma cells were amplified, and freeze preserved.

Figure 3A:
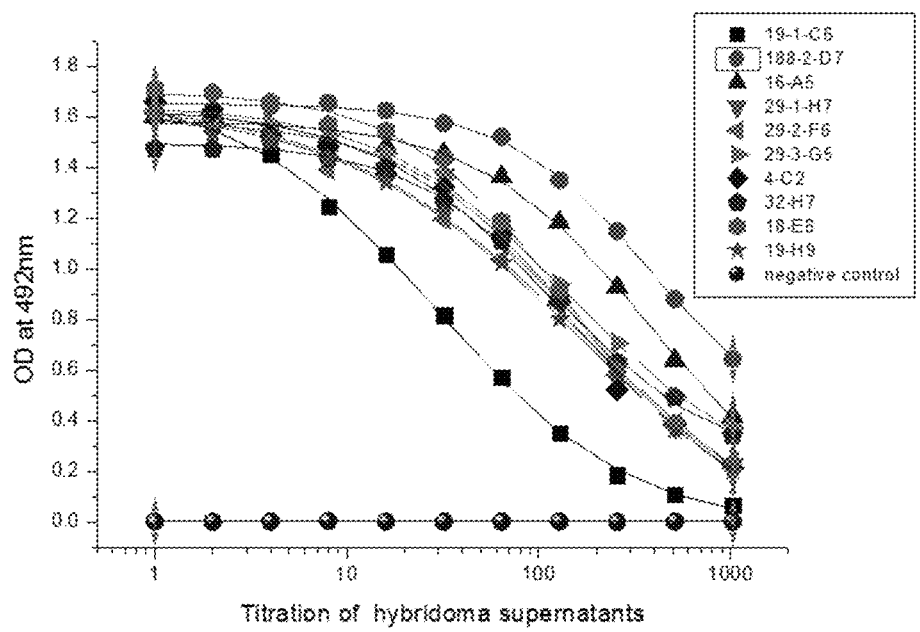
FIG. 3A is a schematic diagram showing the screening results from mouse hybridoma culture supernatant samples, as in Example 1 of the present invention. The screening method is an ELISA using a 96-well plate coated with the recombinant human TIGIT extracellular protein, wherein the unfused SP2/0 myeloma cell culture supernatant serves as the negative control sample.

FIG. 3A shows the re-tested results of supernatants from 11 mouse hybridoma cells, all are positive as detected by the ELISA assay.

Step 4. Sub-Cloning of the Positive Hybridoma Cell by Limited Dilution Method

The positive hybridoma cells obtained from the above preliminary screening were diluted with RPMI-1640-10% FCS medium to 1-10 cells per well and coated in a 96-well cell culture plate, incubated at 37° C. in an incubator with 5% $CO_2$ for 2-3 weeks. After the clones were grown-up, the supernatants were taken and used for ELISA assay for detection and identification of the anti-TIGIT antibody.

Figure 3B:
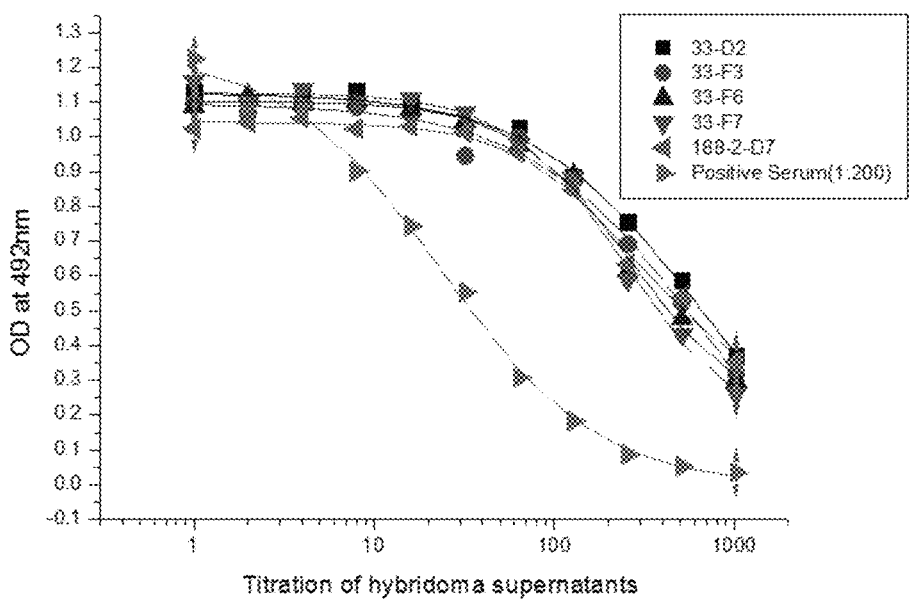
FIG. 3B is a schematic diagram showing the screening results from mouse hybridoma culture supernatant samples, as in Example 1 of the present invention. The screening method is an ELISA using a 96-well plate coated with the recombinant human TIGIT extracellular protein, wherein the serum from the mouse immunized with TIGIT antigen serves as the positive control sample is

FIG. 3B shows the representative ELISA results of the supernatants from subclone cell lines. The supernatant samples from hybridoma subclones 33-D2, 33-F3, 33-F6, 33-F7, and 188-2-D7 all showed a high titer of anti-TIGIT antibodies.

Step 5. Expansion Culture of the Hybridoma Subclones in Serum-Free Medium, Isolation and Purification of the Antibodies from Supernatants In this example, the aforementioned hybridoma subclone 33D2 and the hybridoma subclone 188-2-D7 were cultured in a serum-free medium for further expansion, and about 1 L of hybridoma supernatants were collected from each subclone. The supernatants were used for the purification of the antibody protein by using Protein G Sepharose (GE product) (refer to instructions). The purified antibody protein was analyzed by SDS-PAGE (Sodium Dodecyl sulfate-polyacrylamide Gel Electrophoresis).

Figure 4:
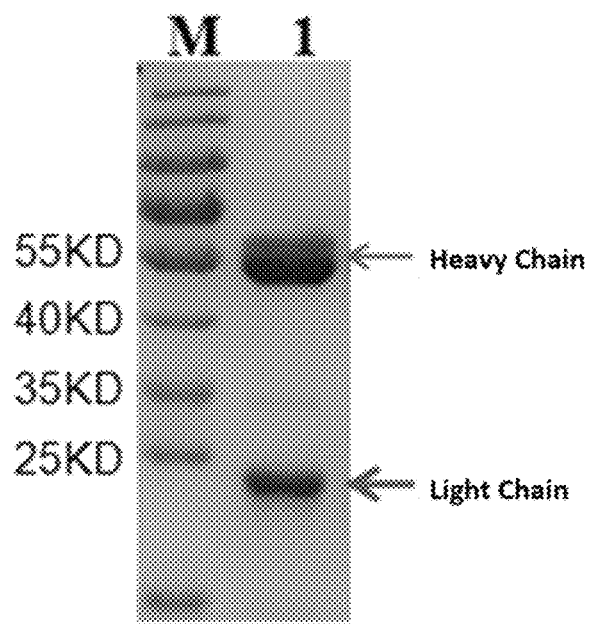
FIG. 4 is an SDS-PAGE gel showing the analysis result of purified mouse 33D2 antibody protein after DTT reduction (DTT-denatured), as in Example 1 of the present invention.

FIG. 4 shows the SDS-PAGE analysis of the purified murine 33D2 antibody protein after DTT reduction (DTT-denatured). As shown in FIG. 4, the reduced antibody protein sample presents two bands: the upper one is the antibody heavy chain, and the lower one is the antibody light chain.

Example 2. Detecting the Binding of Murine Monoclonal Antibody to TIGIT and Other Immune-Related Proteins by ELISA The binding activities of purified 33D2 mAb and 188-2-D7 mAb to TIGIT and other related proteins were analyzed by an ELISA method.

The basic steps of ELISA are as follows: purified murine 33D2 mAb and 188-2-D7 mAb were diluted to 1 μg/mL, separately added to a 96-well plate pre-coated with the recombinant TIGIT-His protein or other immune-related genes Fc fusion protein (including 12 antigens such as CD28, B7-1, CTLA4, CD3, PD-1, PD1H (PD2), PD-L1, PD-L2, etc., coating concentration of each antigen was 2 μg/mL). After incubation at 37° C. for 1 h and washing, HRP-labeled Goat anti-Mouse IgG (Jackson, USA) was added to each well of the 96-well plate, after incubation at 37° C. for 1 h again and washing, OPD substrate was added to each well.

Table 2 shows the representative results of the binding of the purified 33D2 mAb, 188-2-D7 mAb to TIGIT and other immune-related proteins, as detected by ELISA (OD at 492 nm):

TABLE 2

Binding of murine 33D2 mAb to TIGIT and other immune-related proteins (OD at 495 nm)

| mAb | TIGIT- | Sirpa- | PV1- | PD-1 | PD1H | PDL1 | PDL2 | CD3 | CD28 | CTLA4 | B7-1 | BTLA |
|---|---|---|---|---|---|---|---|---|---|---|---|---|
| 33D2 | 1.013 | 0.01 | 0.05 | 0.01 | 0.01 | 0.00 | 0.04 | 0.01 | 0.03 | 0.02 | 0.03 | 0.01 |
| 188-2-D7 | 0.885 | 0.01 | 0.04 | 0.01 | 0.01 | 0.00 | 0.04 | 0.06 | 0.02 | 0.02 | 0.02 | 0.01 |

Figure 5:
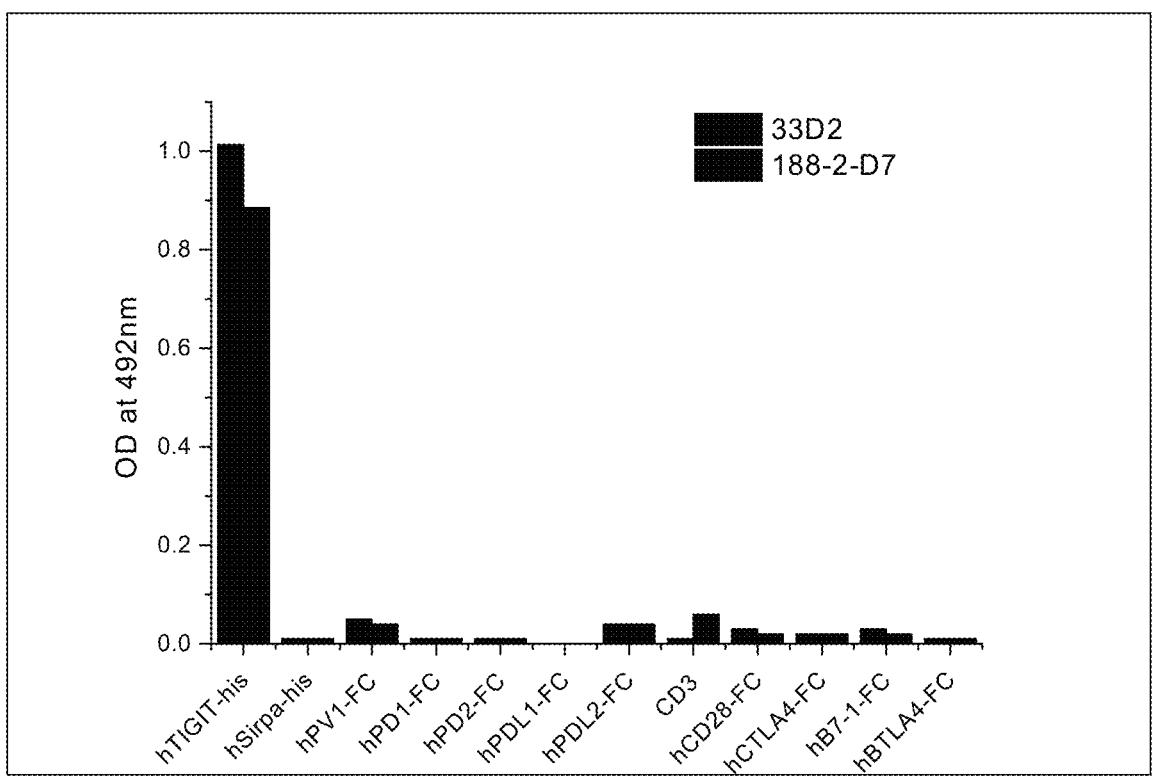
FIG. 5 is a schematic diagram showing the binding of purified murine monoclonal antibody to a recombinant human TIGIT protein or other immune-related recombinant protein coated in 96-well plate and detected by ELSIA method, as in in Example 2 of the present invention.

FIG. 5 is a bar chart corresponding to the OD value at 495 nm as shown in Table 2. As shown in the figure, both 33D2 mAb and 188-2-D7 mAb can specifically bind to human TIGIT protein, but not other immune-related proteins including PD-1, CD28, B7, CTLA-4, CD3, PD-L1, PD-L2, etc.

Example 3. Detecting the Binding of Murine Monoclonal Antibody to CHO Cells Transfecting with Human TIGIT Gene (CHO/TIGIT) by Flow Cytometry In this example, supernatants of the murine hybridoma cell line 33D2 were used as the primary antibody and FITC fluorescence-labeled Goat anti-Mouse IgG antibody was used as the detecting antibody and the binding of murine 33D2 mAb to CHO cells stably expressing the human TIGIT gene (CHO/TIGIT) was detected and analyzed by flow cytometry. For this propose, CHO/TIGIT cells were incubated with samples containing either mouse IgG (negative control sample, isotype control), murine 33D2 supernatant, and serum from TIGIT antigen immunized mouse (positive control sample, Immu. sera, 1:200 dilution) at 4° C. for 30 min and washed with PBS-1% BSA solution, then FITC-labeled Goat anti-Mouse IgG (Sigma Company) was added and incubated at 4° C. for 30 min. After being washed with PBS-1% BSA solution again, the samples were loaded to Biosciences Accuri C6 flow cytometry (BD, USA) for detection of the binding.

Figure 6:
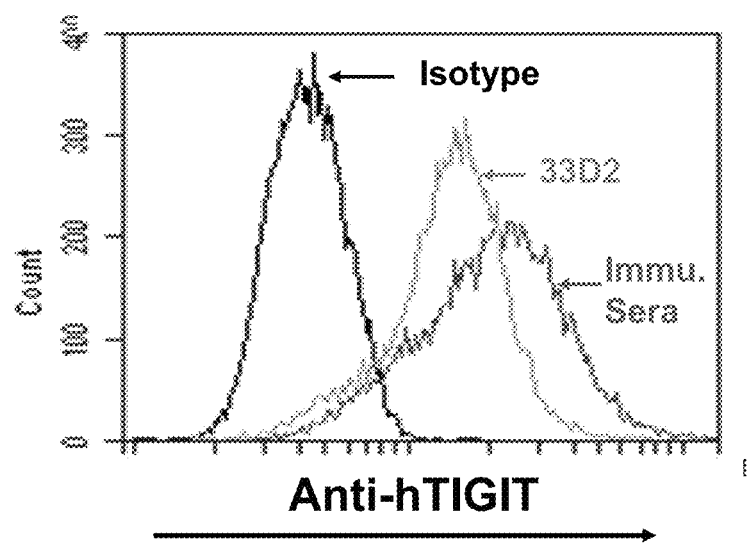
FIG. 6 is a schematic diagram showing the binding of the purified mouse antibody sample to CHO cells stably transfecting with the human TIGIT gene (CHO/TIGIT), as detected and analyzed by flow cytometry in Example 3 of the present invention.

FIG. 6 is a representative result detected by the flow cytometry. As shown in FIG. 6, compared with the mouse IgG negative control sample (isotype control), both the TIGIT-immunized mouse serum sample (immu. sera) and the test sample (33D2 mAb supernatant, 33D2) showed specifically bind to CHO/TIGIT cells. The binding intensity of 33D2 mAb is similar to that of the mouse positive serum control.

Example 4. Detecting the Binding of Murine Antibody to Peripheral Blood Lymphocyte from Human TIGIT Gene Knock-In Mouse by Flow Cytometry In this example, lymphocytes were isolated from peripheral blood from either C57/B6 wild-type mice or mice with human TIGIT gene knock-in (Human TIGIT knock-in mice were from Biocytogen Biological Company), and incubated with the murine 33D2 supernatant followed by FITC-labeled polyclonal rabbit anti-mouse IgG (PE-labeled anti-mouse CD3e was added for T lymphocyte labeling), the binding of 33D2 mAb to mouse lymphocytes in mice was detected and analyzed by flow cytometry. The methods are as follows:

1) 100 μL anti-coagulant was added into an EP tube in advance, 150 μL blood was abstracted from the tail vein of C57/B6 wild-type mice and human TIGIT gene knock-in mice respectively, and mixed together; hemolysin (BD Company) was added and reacted for 10 min at room temperature (keep away from light); After centrifugated, the supernatant was discarded, and the TIGIT humanized mouse samples were divided into three equal parts, centrifugated; wherein two tubes of them were FITC single-positive tube and PE single-positive tube respectively, and one tube was a test tube.

2) The supernatant was discarded, and diluent was added to PE single-positive tube; FITC single-positive tube and other detection tubes were added with TIGIT mAb33-D2 hybridoma supernatant at 500 μL/well and reacted for 30 min at 4° C. Centrifugated at 1500 rpm for 5 min; the supernatant was discarded and washed with 1% BSA once; wherein FITC-labeled Polyclonal Rabbit anti-mouse IgG was added to FITC single-positive tube, PE-labeled anti-Mouse CD3e (1:25) was added to PE single-positive tube, PE-labeled anti-Mouse CD3e and FITC-labeled Polyclonal Rabbit anti-mouse IgG were added to the test tube at 10011 L/well, reacted at 4° C. for 30 min. Centrifugated at 1500 rpm for 5 min, washed once with 1% BSA, and the cells were re-suspended with 150 uL 1% BSA, then the samples were loaded into the Biosciences AccuriC6 flow cytometer (BD) for detection.

Figure 7:
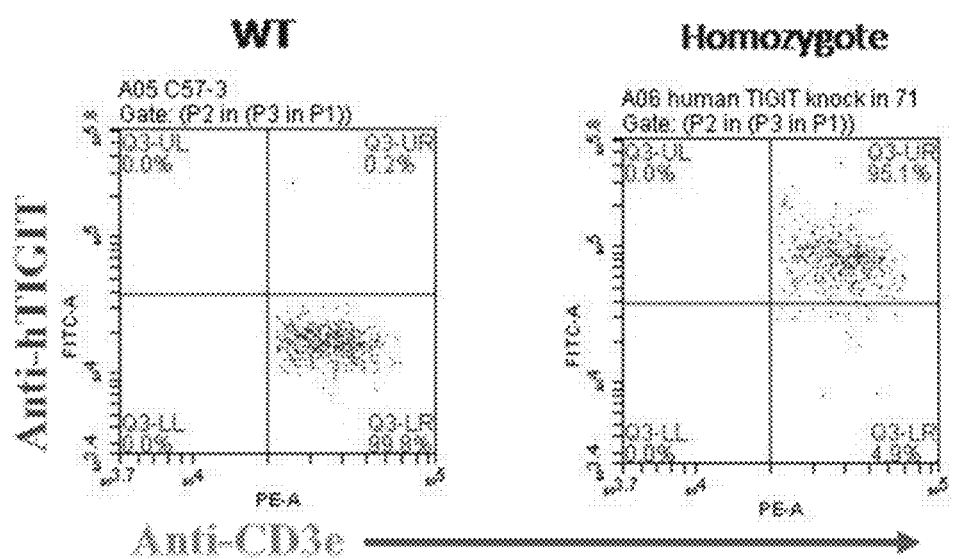
FIG. 7 is a schematic diagram showing the binding of the purified mouse antibody sample to peripheral blood lymphocyte (PBL) isolated from wild-type C57B/L mice or human TIGIT gene knock-in mice, as detected and analyzed by flow cytometry in Example 4 of the present invention.

FIG. 7 is a schematic diagram of the representative results detected by flow cytometry. As shown in FIG. 7, the 33D2 mAb can specifically bind to human TIGIT gene knock-in mouse lymphocytes, but not to C57/B6 wild-type mouse lymphocytes.

Example 5. Inhibiting the Binding of TIGIT to its Ligand by a Competitive ELISA

One of the methods to detect the biological activity of the anti-TIGIT mAbs in vitro is to use a competitive ELISA to test whether it can inhibit the interaction between TIGIT to its ligands such as CD155 (PVR).

For this propose, the procedures of the competitive ELISA are as follows:

1) Coated a 96-well plate with the recombinant human TIGIT-his extracellular membrane protein (Beijing SinoBiological Company) (coating concentration: 2 μg/mL, 50 μL/well), overnight at 4° C.;

2) After washing with PBS solution and blocking with 5% milk (diluted in PBS-0.1% tween20 solution) at room temperature for 1 hour, a fixed amount of biotin-labeled CD155 (PVR)-Fc protein (ACRO Biosystems) with different amounts of 33D2 mAb or non-related antibodies (such as anti-VEGF monoclonal antibody hPV19) were added into the wells of the plate and incubated at 37° C. for 1 h;

3) After washing with PBS-T, HRP-labeled Avidin (1:5000) was added and incubated at 37° C. for 1 h;

4) After washing with PBS-T, color developing solution ((o-phenylenediamine)-3% hydrogen peroxide) was added and incubated at room temperature for 5-10 min;

5) 1M HCL was then added to terminate the reaction, and the OD value at 492 nm of each well of the plate was detected by a microplate reader.

Figure 8:
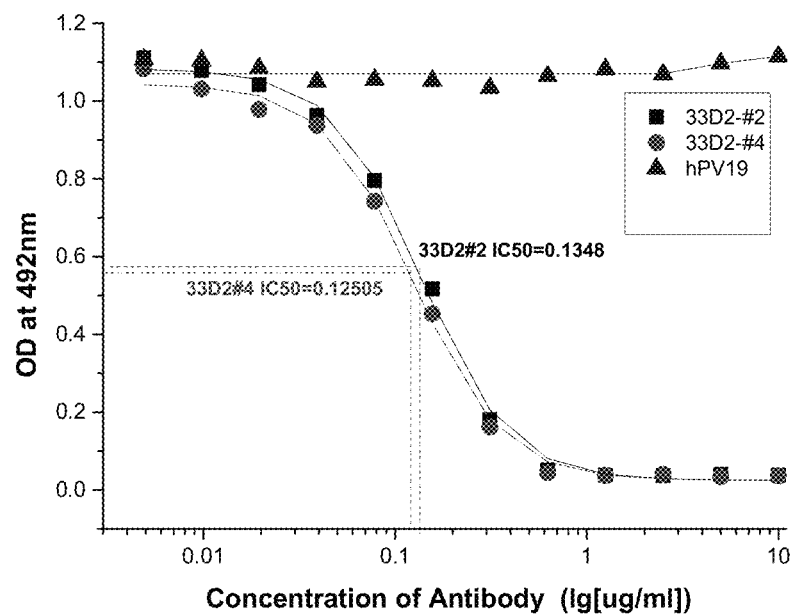
FIG. 8 is a schematic diagram showing the competitive blocking the binding of CD155 to TIGIT pre-coated in the 96-well plate by the monoclonal antibody sample, in a competitive ELISA assay as in Example 5 of the present invention.

Table 3 and FIG. 8 are the representative results showing the blocking effect of 33D2 mAb to the binding of CD155 to TIGIT protein.

TABLE 3

Blocking effect by competitive ELISA in vitro

| mAb concent. µg/mL | OD at 492 nm | | |
|---|---|---|---|
| | 33D2-sample #2 | 33D2-sample #4 | hPV19 |
| 10 | 0.038 | 0.036 | 1.115 |
| 5 | 0.040 | 0.034 | 1.097 |
| 2.5 | 0.037 | 0.040 | 1.069 |
| 1.25 | 0.038 | 0.037 | 1.082 |
| 0.625 | 0.051 | 0.045 | 1.065 |
| 0.312 | 0.181 | 0.162 | 1.034 |
| 0.156 | 0.517 | 0.453 | 1.052 |
| 0.078 | 0.796 | 0.742 | 1.055 |
| 0.039 | 0.963 | 0.937 | 1.050 |
| 0.019 | 1.042 | 0.978 | 1.085 |
| 0.010 | 1.079 | 1.031 | 1.104 |
| 0.005 | 1.111 | 1.083 | 1.107 |

FIG. 8 is a fitted line graph using graphing software (OriginPro 9.0) based on the raw data or OD at 495 nm in Table 3.

As shown in FIG. 8, in the samples with a fixed concentration of biotin-labeled CD155-Fc protein and different concentrations of 33D2 mAb (33D2-sample #2, 33D2-sample #4), the OD value in each well is inversely proportional to the amount of antibody protein added, that is, the higher the amount of 33D2 mAb added, the lower the OD value; while the amount of non-related mAb (hPV19, anti-VEGF mAb) added has little effect on the OD value of each well. These results show that 33D2 mAb can block the binding of TIGIT to its receptor (CD155) in vitro, and its average half-inhibitory concentration ($IC_{50}$ value) measured according to the fitted graph is 0.13 µg/ml (converted to molar concentration, its mean value $IC_{50}$ is 0.867 nM). The $IC_{50}$ results are shown in Table 4.

TABLE 4

Half-inhibitory concentration ($IC_{50}$ value)

| Sample ID | IC50 (µg/mL) | IC50 (nM) |
|---|---|---|
| 33D2-sample #2 | 0.135 | 0.900 |
| 33D2-sample#4 | 0.125 | 0.833 |
| Average | 0.130 | 0.867 |

Example 6. Cloning of the Gene Encoding the Variable Region of Murine 33D2 Antibody Herein, the total RNA was extracted from the mouse 33D2 hybridoma cells and used as a template together with the degenerate primers to clone, amplify, and obtain the cDNA gene fragments of the m33D2 antibody heavy chain variable region and light chain variable region respectively by reverse transcription-polymerase chain reaction (RT-PCR) method (Wang Y, et al. Degenerated primer design to amplify the heavy chain variable region from immunoglobulin cDNA. BMC Bioinformatics. 2006; 7 Suppl (4): S9).

Wherein the cDNA gene cloning steps were as follows:
Step 1. The total RNA was extracted from the mouse m33D2 hybridoma cells with an RNA extraction reagent (RNAiso Plus, Takara);
Step 2. cDNA template was obtained in the Eppendorf tube by RT-PCR method.
Wherein, the sequence of the RT-PCR primer (33-D2-L) for murine 33D2 antibody light chain variable region was TGT CGT TCA CTG CCA TCA AT (SEQ ID NO: 1)
Wherein, the sequence of the RT-PCR primer (33-D2-H) for murine 33D2 antibody heavy chain variable region was GCA AGG CTT ACA ACC ACA ATC (SEQ ID NO: 2);
RT-PCR reaction system was as follows:

| | |
|---|---|
| Primers | 2 µl |
| RNA template | 30 µl |
| Incubated at 70° C. for 10 minutes, then stayed on the ice for 2 minutes; Followed by: | |
| 5 × RT-PCR reaction buffer solution | 10 µl |
| dNTPs | 5 µl |
| Reverse Transcriptase | 1.5 µl |
| Distilled water | 1.5 µl |
| Total volume | 50 µl |

Reacted at 42° C. for 1 hour, then increased the temperature to 70° C., after 15 minutes of inactivation, the cDNA was obtained and stored at −20° C. for later use.

Step 3: PCR cloning and amplification of murine 33D2 antibody light chain variable region gene and heavy chain variable region gene A pair of primers used to clone and amplify the 33D2 antibody light chain variable region gene were:

```
Forward primer:
                                    (SEQ ID NO: 3)
GAC ATC CAG ATG A Reverse primer:
                                    (SEQ ID NO: 4)
CTG AGG CAC CTC CAG ATG TT
```

While a pair of primers used to clone and amplify the 33D2 antibody heavy chain variable region gene were:

```
Forward primer:
                                    (SEQ ID NO: 5)
GTG CAG TCT GGA CCT GA Reverse primer:
                                    (SEQ ID NO: 6)
GTG CTG GAG GGG ACA GTC ACT
```

DNA products from PCR amplification were analyzed by electrophoresis in 1.5% agarose gel. When electrophoresis is over, the nucleotide sequences of the DNA of antibody light and heavy chain variable regions were obtained by cutting and sequencing the isolated DNA bands. The nucleotide sequence of DNA of the murine antibody light chain variable region was set forth in SEQ ID NO: 7, and the amino acid sequence of DNA of the antibody light chain variable region inferred from the DNA nucleotide sequences was set forth in SEQ ID NO: 8. The amino acid sequences of complementarity-determining regions (CDR) CDR1, CDR2, and CDR3 of the light chain antigen were set forth in SEQ ID NO: 9, SEQ ID NO: 10, and SEQ ID NO: 11, respectively.

The nucleotide sequence of DNA of the murine antibody heavy chain variable region was set forth in SEQ ID NO: 12, and the amino acid sequence of DNA of the antibody heavy chain variable region inferred from the DNA nucleotide sequence was set forth in SEQ ID NO: 13. The amino acid sequences of complementarity-determining regions (CDR) CDR1, CDR2, and CDR3 of the heavy chain antigen were set forth in SEQ ID NO: 14, SEQ ID NO: 15, and SEQ ID NO: 16, respectively.

Example 7. Construct of Human-Mouse Chimeric Antibody (c33D2) Based on Murine Antibody 33D2

Murine 33D2 antibody light and heavy chain variable region genes obtained by cloning and amplification in Example 6 were fused respectively with a human kappa light chain constant region (C-domain) and a human IgG4 heavy chain constant region fragment gene to obtain the human-mouse chimeric light chain gene (c33D2L) and the human-mouse chimeric heavy chain gene (c33D2H). After that, the light and heavy chain chimeric genes were respectively cloned into the expression plasmid pcDNA3.1, then transferred into E. coli to amplify, and separated to obtain plenty of expression plasmids containing the human-mouse chimeric antibody gene.

The sample of the expression plasmid containing the human-mouse chimeric antibody light chain gene and sample of the expression plasmid containing the human-mouse chimeric antibody heavy chain gene were combined, mixed with Fugen-6 liposomes (Roche), and transfected into CHO cells. Two days after cells transfection, the culture supernatants were collected and transferred to a 96-well plate coated with human TIGIT protein, HRP-labeled Goat anti-Human IgG (Fab specific) antibody (Sigma-Aldrich) was added as a secondary detection antibody to detect the binding of the chimeric antibody (c33D2) in the supernatant to human TIGIT protein by ELISA. The representative ELISA results were shown in the following Table 5:

TABLE 5

Binding of cell culture supernatants from cells transiently transfected with chimeric antibody (c33D2) to human TIGIT protein by ELISA

| Supernatant Dilution Fold | 1 | 2 | 4 | 8 | 16 | 32 | 64 | 128 |
|---|---|---|---|---|---|---|---|---|
| OD at 492 | 0.6048 | 0.3277 | 0.1781 | 0.1044 | 0.058 | 0.0345 | 0.0201 | 0.0132 |

The results in Table 5 demonstrated that supernatants from CHO cells transfected with the human-mouse chimeric antibody gene c33D2 expressing plasmid can specifically bind to human TIGIT protein.

The above-transfected cells culture supernatants were centrifugated and filtered with a 0.45 μm filter membrane, then loaded to a Protein-A chromatography affinity column (Protein-A Sepharose Fast Flow, GE, USA). After this purification, a pure human-mouse chimeric antibody (c33D2) protein was obtained.

Example 8. Humanization of Murine Antibody 33D2 by Genetic Engineering

Upon confirmation of the high-affinity binding of human-mouse chimeric antibody c33D2 to human TIGIT protein by ELISA, a series of genetic engineering and cloning methods such as PCR were used to transplant the antigen complementarity-determining regions (CDRs) gene fragments from the chimeric antibody light chain and heavy chain to the corresponding human Kappa-light chain variable framework regions (FR) and IgG4-heavy chain variable framework region (FR), to obtain a humanized version of the antibody h33-D2.

2) Humanization of 33D2 Antibody Light Chain

Through amino acid sequence analysis, the expression product of the first V germline Gene of the human immunoglobulin Kappa light chain (IgKV1-9, NCBI Gene ID: 28941) was identified to have the highest homology with the light chain variable region of the 33D2 antibody. Accordingly, the light chain framework region (FR) of the 33D2 was replaced with the homologous sequence of human IgKV1-9, then the replaced variable region gene was fused with the sequence coding the light chain constant region of human immunoglobulin IgG-Kappa, and finally, the humanized light chain coding gene (h33D2-L) was successfully obtained. Wherein the amino acid sequence of the light chain variable region of the humanized h33D2 antibody was shown in SEQ ID NO:17, and its nucleotide sequence was shown in SEQ ID NO: 18.

2) Humanization of 33D2 Antibody Heavy Chain

Through amino acid sequence analysis, the expression product of the third V germline Gene of the human immunoglobulin heavy chain (IgHV1-2, NCBI Gene ID: 28474) was identified to have the highest homology with the heavy chain of 33D2. Accordingly, the heavy chain framework region (FR) of 33D2 was replaced with the homologous sequence of human IgHV1-2, at the same time, in order to reduce the binding of the humanized antibody to the immunoglobulin-Fc receptor (FcR) in the body and reduce its antibody-dependent cellular cytotoxicity (ADCC) to kill TIGIT positive immune cells (lymphocytes), the variable region gene of the humanized 33D2 antibody was intentionally fused with the coding sequence of the heavy chain constant region of human immunoglobulin IgG4, and the amino acid at position 228, proline, in the hinge region, was replaced with serine (S228P). After a series of genetic engineering and transformations, a full-length h33D2 antibody heavy chain containing the humanized heavy chain variable region and the constant region (S228P) of the human IgG4-heavy chain was successfully obtained. Wherein the amino acid sequence of the heavy chain variable region of the humanized h33D2 antibody was shown in SEQ ID NO: 19, and the nucleotide sequence thereof was shown in SEQ ID NO: 20.

Example 9. Construct of Cells Expressing and Secreting Humanized 33D2 Antibody, Isolation and Purification of the Humanized Antibody Protein The humanized heavy chain gene (h33D2-H) and humanized light chain gene (h33D2-L) in Example 8 were cloned separately into the expression vector pQY-Hygro, then transferred into E. coli, was amplified and isolated to obtain a recombinant plasmid expressing humanized 33D2 antibody. After that, the recombinant plasmid was transiently transfected into CHO-S cells, respectively. 48-hour after transfection, the cell culture supernatant in the well were collected. TIGIT-his protein was used as coating antigen, HRP-labeled Goat-anti-human-IgG antibody was used as a secondary detection antibody (purchased from Shanghai Xitang Biological Company), OPD was used as a chromogenic substrate to detect the binding activity of the antibody in the supernatant of the transfected cells to human TIGIT antigen by direct ELISA.

Table 6 shows one of the representative ELISA test results.

TABLE 6

Detection of the Binding of supernatants from transiently transfected CHO cells to human TIGIT protein by ELISA

| Supernatant Dilution-fold | OD at 492 nm | | |
|---|---|---|---|
| | c33D2-light chain and c33D2-heave chain | h33D2-light chain and h33D2-heave chain | Negative control |
| 2 | 0.752 | 0.882 | 0.105 |
| 4 | 0.458 | 0.604 | 0.038 |
| 8 | 0.267 | 0.367 | 0.015 |
| 16 | 0.146 | 0.206 | 0.008 |
| 32 | 0.073 | 0.116 | 0.007 |
| 64 | 0.042 | 0.069 | 0.007 |
| 128 | 0.028 | 0.035 | 0.007 |
| 256 | 0.036 | 0.027 | 0.129 |

Figure 9:
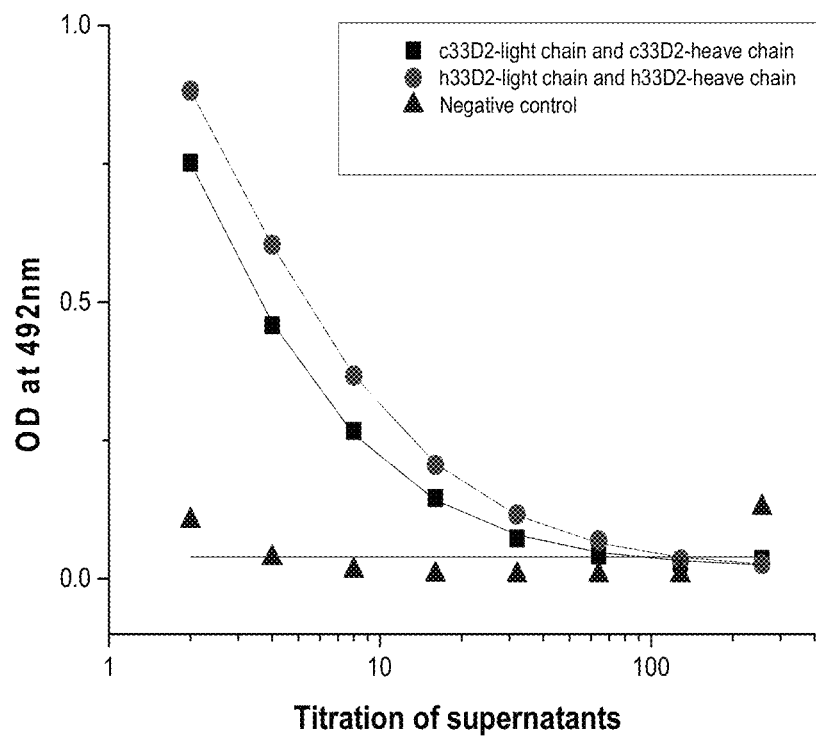
FIG. 9 is a schematic diagram showing the binding of cell culture supernatant samples from CHO-S transiently transfected with the expression vector for recombinant humanized antibody h33D2 or recombinant chimeric antibody c33D2, to human TIGIT protein coated in a 96-well plate, by ELISA assay in Example 9 of the present invention.

FIG. 9 is a fitted graph using graphing software (Origin-Pro 9.0) based on the raw data or OD at 492 nm in Table 6. The results show that the humanized h33D2 antibody (IgG4-kappa) can specifically bind to human TIGIT protein, and the binding activity (or affinity) is similar to that of the human-mouse chimeric c33D2 antibody.

The above-transfected cells were then suspended in serum-free medium and cultured for cloning and screening. A number of CHO cell clones that stably and efficiently expressing the humanized h33D2 antibody protein were successfully obtained.

After that, one cell line was selected and expanded in serum-free culture medium, and the culture supernatants were collected. The supernatants were centrifugated and filtered with a 0.45 μM filter membrane. After multiple separations and purification steps including loading into a protein A affinity chromatography column (protein A-Sepharose Fast Flow, GE, USA), ion exchange column, virus removal/inactivation, and sterilization by filtration (0.22 μM filter membrane), a final product of humanized antibody (h33D2) with a high purity (over 99% protein purity) was obtained. The purified humanized antibody (h33D2) was dissolved in sterile saline solution and stored at a low temperature (below −20° C.).

Example 10. Antibody Affinity Kinetics Assay

Biosensor (Fortebio-OCTET RED96, PALL Company) was used to in real-time monitor and determine the binding affinity and kinetic curves of the purified humanized 33D2 mAb to TIGIT antigen. The detection method and results were as follows:

3. Biosensor and Preparation of Experimental Material Solution
Biosensor chip: Coated with anti-human Fab-CH1 2nd Generation antibody (FAB2G, ForteBio, 1802083).
Preparation of Experimental Material Solution:
1.1. Kinetic binding (KB) buffer: 0.1% BSA 0.05% Tween 20 was dissolved in commercial PBS, pH7.2.
1.2. Antibody working solution: humanized 33D2 mAb sample was prepared to 10 μg/mL with KB buffer.
1.3. Antigen working solution: recombinant human TIGIT-His protein (Beijing SinoBiological Company, Product No. 10917-H08H) was prepared with KB buffer to three concentrations of 100 nM, 25 nM, and 6.25 nM.
2. Detection Method and Procedure
2.1. Open the Fortebio instrument and related software, and select Advance Kinetics experiment mode;
2.2. The analysis procedure was carried out according to Table 7:

TABLE 7

| Assay step | Assay time (s) | Sample |
|---|---|---|
| Baseline | 60 | KB buffer |
| Loading | 400 | mAb 33-D2 |
| Baseline | 60 | KB buffer |
| Association | 400 | TIGIT-His |
| Dissociation | 600 | KB buffer |

Figure 10:
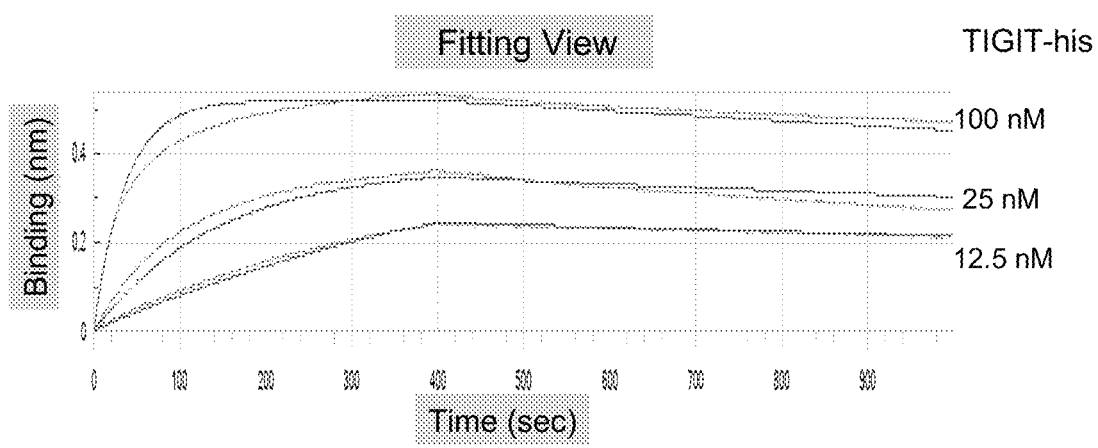
FIG. 10 is an association/dissociation curve showing the interaction of 33D2 mAb with TIGIT antigen by the instrument, as in Example 10 of the present invention.
Figure 11A:
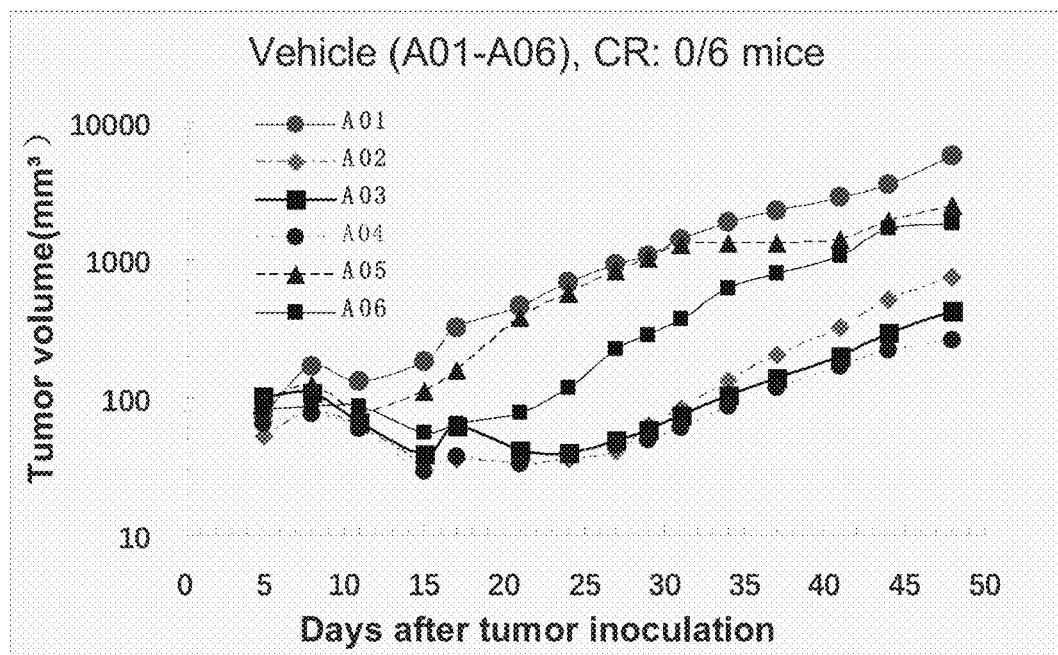
FIG. 11A shows a trend of tumor growth in volume in each animal in the saline control treatment group (Negative control, Group A) in a subcutaneous implantation murine MC38 colon cancer model in the human TIGIT/PD-1 gene double knock-in mice, as in Example 11 of the present invention.
Figure 11B:
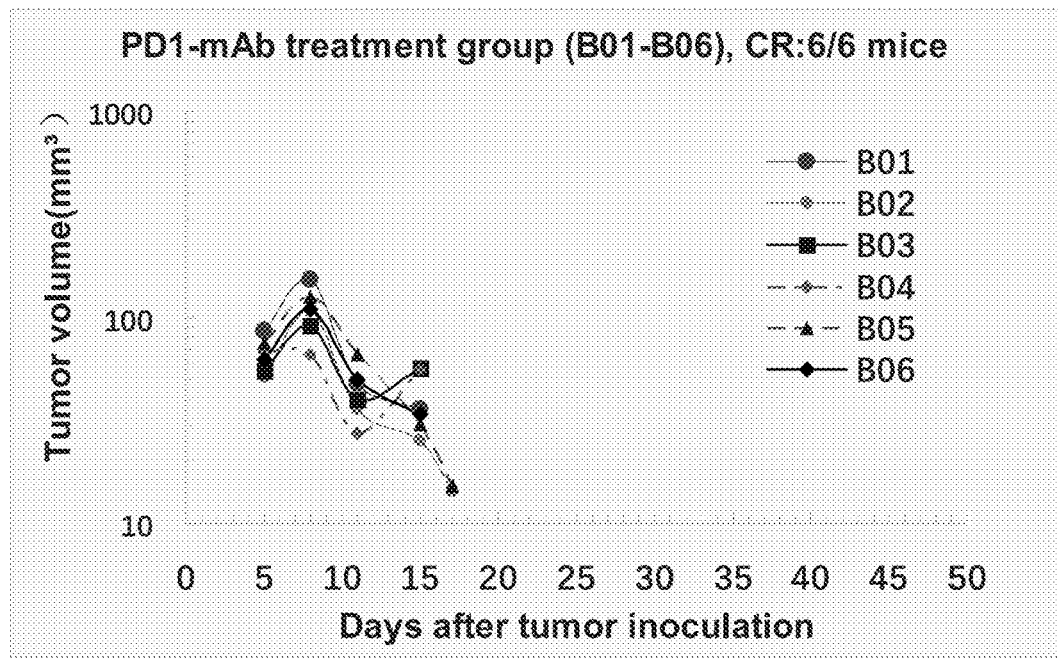
FIG. 11B shows a trend of growth in volume in each animal in the PD-1 monoclonal antibody treatment group (Group B) in a subcutaneous implantation murine MC38 colon cancer model in the human TIGIT/PD-1 gene double knock-in mice, as in Example 11 of the present invention.
Figure 11C:
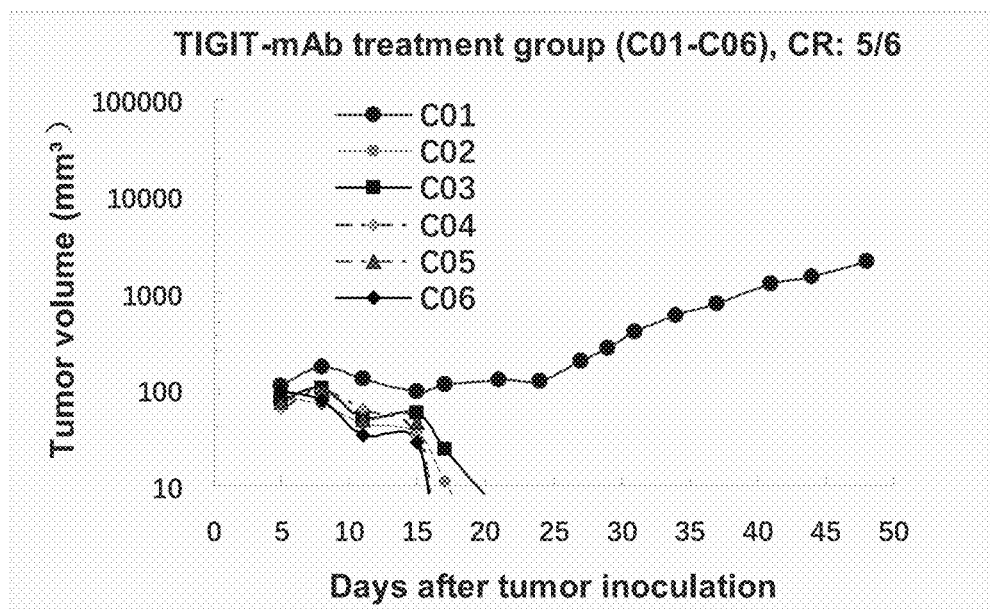
FIG. 11C shows a trend of tumor growth in volume in each animal in a TIGIT mAb treatment group (Group C), in a subcutaneous implantation murine MC38 colon cancer model in the human TIGIT/PD-1 gene double knock-in mice, as in Example 11 of the present invention.
Figure 11D:
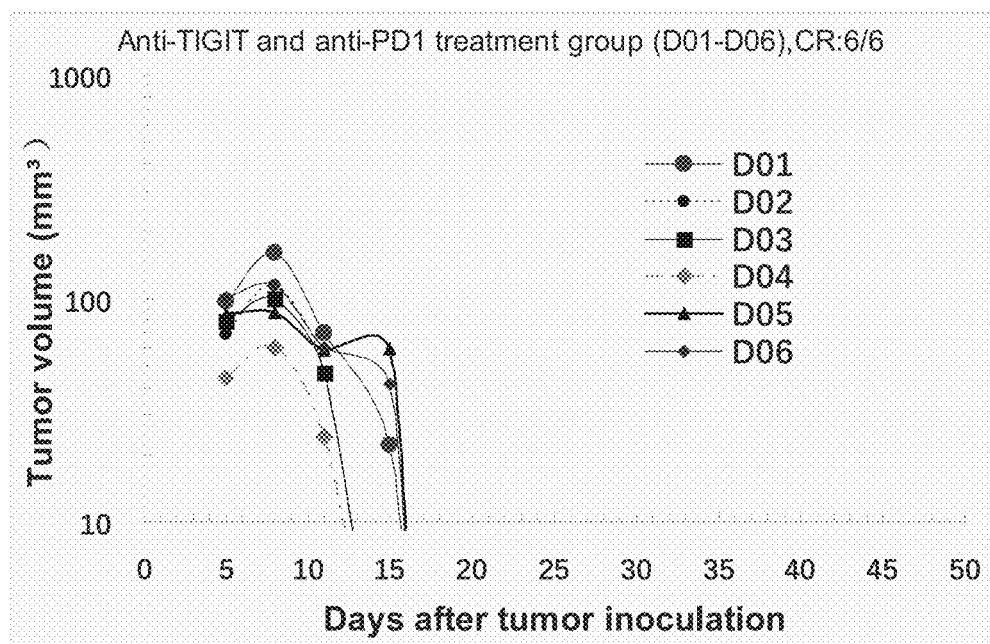
FIG. 11D shows a trend of tumor growth in volume in each animal in a PD-1 mAb and TIGIT-mAb combination treatment group (Group D) in a subcutaneous implantation murine MC38 colon cancer model in the human TIGIT/PD-1 gene double knock-in mice, as in Example 11 of the present invention

4. Experimental Results
FIG. 10 shows the dynamic association/dissociation curve of the different concentrations of TIGIT antigen binding to the humanized 33D2 mAb captured in the sensor. The 0 s to 400 s represented the association, 400 s to 1000 s represented the dissociation, and the three curves from top to bottom represented the binding curves of humanized 33D2 mAb to TIGIT-His at 100 nM, 25 nM, and 12.5 nM concentrations, respectively. Table 8 shows the affinity kinetics constants: the results show that humanized 33D2 mAb had a high-binding affinity to TIGIT, and the binding affinity was determined to be 0.843 nM.

TABLE 8

Affinity kinetics detected (monovalent binding)

| Loading Sample ID | Association Sample ID | KD (Mole) | Kon (1/Ms) | Kdis (1/s) | $R^2$ |
|---|---|---|---|---|---|
| Humanized 33D2 mAb | TIGIT-His (monomer) | $8.43 \times 10^{-10}$ | $2.73 \times 10^5$ | $2.30 \times 10^{-4}$ | 0.983 |

(Table 8 shows the value of association/dissociation and affinity calculated with Global mode. KD represents the value of affinity, Kon represents the value of the association and Kdis represents the value of the dissociation. $R^2$ represents the correlation coefficient between the fitting curve and the association/dissociation curve. The closer this value is to 1, the closer the fitting result is to the real result)

Example 11. Anti-tumor Efficacy of Anti-TIGIT mAb in Human PD-1 and Human TIGIT Gene Double Knock-In Mice Since 33D2 mAb does not recognize mouse TIGIT, the anti-tumor efficacy cannot be directly tested in normal mice in vivo. Therefore, in this example, mouse colon cancer cells expressing CD155 (MC38-CD155) were specially selected for the in vivo test of the mouse anti-human TIGIT mAb 33D2 in genetically engineered Human PD-1 and Human TIGIT Gene Double Knock-In Mice. 33D2 mAb was administered as a single agent or in combination with mouse anti-human PD-1 monoclonal antibody hAb21 (Stainwei's product) in a series of studies of antitumor efficacy.

The animal experimental study was divided into two phases, in which the experimental model, administration groups, and test results of Phase I were described as follows:

Phase I Study:

Animal Experimental Model and Treatment Groups:

$1\times10^6$ MC38-CD155 mouse colon cancer cells (Provided by Shanghai Model Organisms Center, Inc., originated from C57BL/6 mice) expressing the CD155 gene were inoculated under the right back subcutaneous tissue of human TIGIT/PD-1 double knock-in mice in the same C57BL/6 genetic background (this mouse strain was abbreviated as hPDCD1/hTIGIT, provided by Model Animal Research Center of Nanjing University, which utilized gene homologous recombination through Cas9 method, the human PD-1 gene and TIGIT gene were replaced to the position of mouse endogenous PD-1 gene and mouse endogenous TIGIT gene respectively, thus expressing human PD-1 gene and human TIGIT gene but not mouse PD-1 gene and mouse TIGIT gene). When the tumor volume reached about the size of a grain of rice (about 50-70 $mm^3$, about 5-6 days after tumor cell inoculation), the animals were randomly divided into 4 experimental groups (Table 9):

TABLE 9

Experimental grouping

| Treatment group (dose) | No. of mice |
| --- | --- |
| A: vehicle control (0.9% NaCL) | 6 |
| B: 40 μg anti-PD-1 mAb (hAb21, 2 mg/kg) | 6 |
| C: 40 μg anti-TIGIT mAb(33D2, 2 mg/kg) | 6 |
| D: 20 μg anti-TIGIT mAb (1 mg/kg) + 20 μg anti-PD-1 mAb (1 mg/kg) | 6 |

The animals were given intraperitoneal injection (i.p.) twice a week (once every 3-4 days) from the day of grouping (i.e., 5-6 days after tumor inoculation), for a total of 4 times (continuous 2 weeks). During the period, the general clinical symptoms of the animals were observed every day, and the tumor long diameter (mm) and short diameter (mm) and animal weight were measured every 3-4 days.

The calculation formula of tumor volume was as follows: volume ($mm^3$)=long diameter (mm)×short diameter (mm)× 0.5. If the tumor volume exceeded 4000 $mm^3$ at the time of measurement, the test animals were euthanized.

Animal Test Results:

The test results are summarized in Table 10, Tables 11A-11D, FIGS. 11A-11D, FIG. 12A, and FIG. 12B.

FIGS. 11A-11D show the trend of tumor growth volume in each animal in each treatment group.

Figure 12A:
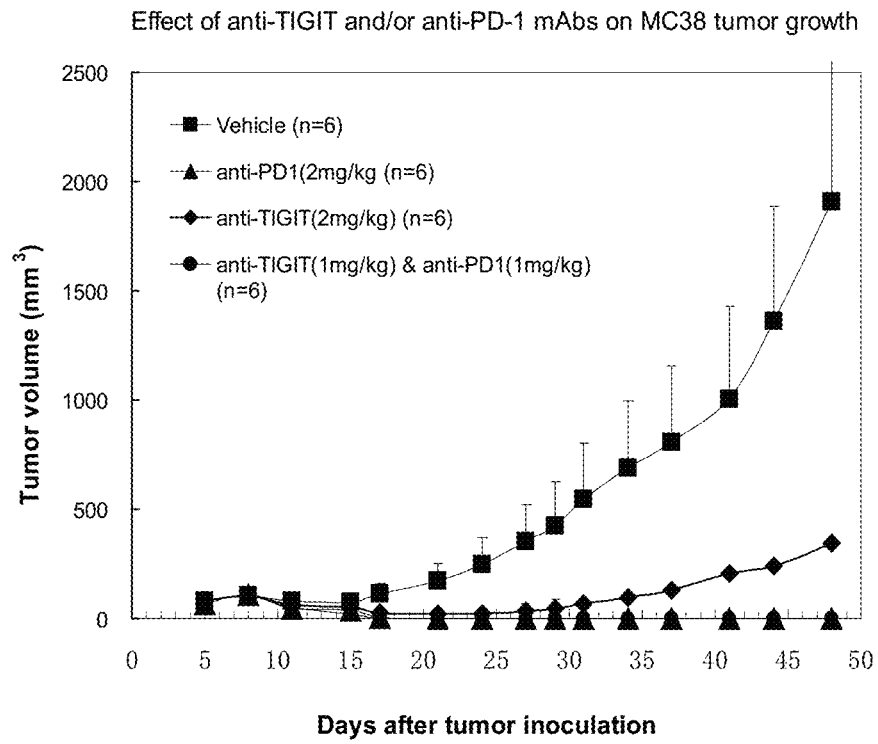
FIG. 12A shows a trend of the average tumor growth volume in each experimental group, as in Example 11 of the present invention.

FIG. 12A shows the trend of average tumor growth volume in each group.

Figure 12B:
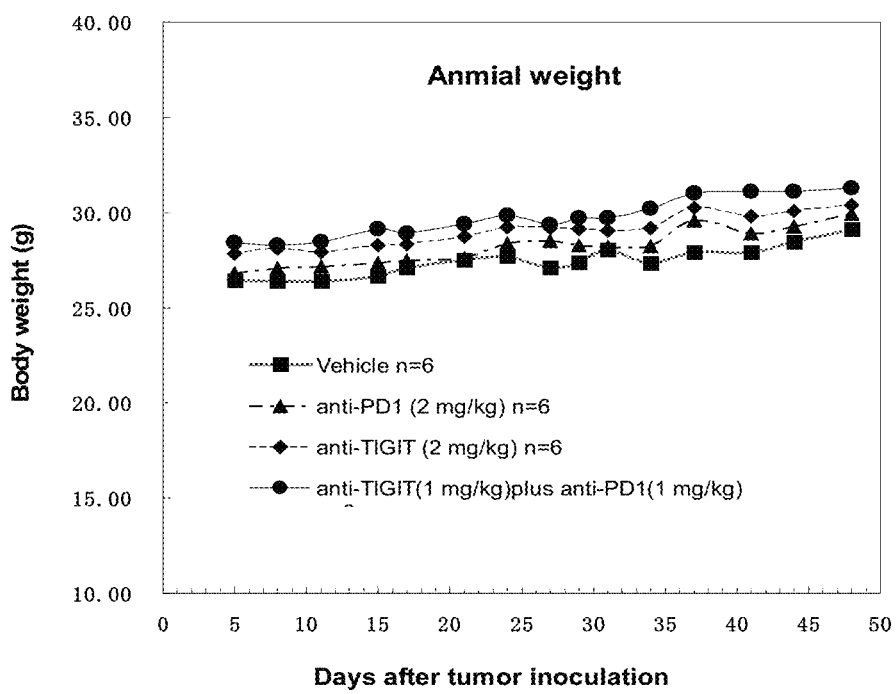
FIG. 12B shows a trend of the average animal body weight in each experimental group, as in Example 11 of the present invention.

FIG. 12B shows the trend of the increasing average body weight of experimental animals in each group.

TABLE 10

Experimental results

| Treatment groups | No. of mice with regressed tumors or complete rejection |
| --- | --- |
| A: vehicle control (0.9% NaCL) | 0/6 |
| B: anti-PD-1 mAb (hAb21, 2 mg/kg) | 6/6 |
| C: anti-TIGIT mAb (33D2, 2 mg/kg) | 5/6 |
| D: anti-TIGIT mAb (1 mg/kg) + anti-PD-1 mAb (1 mg/kg) | 6/6 |

TABLE 11A

Group A (0.9% NaCl, vehicle control group) results
Group A: Tumor volume ($mm^3$) in TIGIT&PD1 double gene knock-in mice treated with 0.9% NaCl (vehicle control group, n = 6)

| Day(*) | A01 Male | A02 Male | A03 Male | A04 Male | A05 Male | A06 Male | Mean ± SE |
| --- | --- | --- | --- | --- | --- | --- | --- |
| 5(1) | 76.52 | 52.26 | 102.81 | 64.39 | 96.33 | 83.43 | 79.29 ± 19.08 |
| 8(4) | 169.96 | 79.11 | 108.54 | 76.67 | 122.16 | 86.37 | 107.13 ± 35.55 |
| 11(7) | 129.96 | 62.22 | 66.06 | 59.42 | 79.15 | 86.69 | 80.58 ± 26.36 |
| 15(11) | 184.62 | 34.02 | 38.81 | 29.03 | 111.49 | 55.08 | 75.51 ± 61.39 |
| 17(13) | 321.75 | 35.89 | 61.60 | 37.30 | 157.34 | 64.48 | 113.06 ± 111.55 |
| 21(17) | 459.07 | 32.88 | 41.62 | 32.87 | 379.61 | 78.38 | 170.74 ± 194.92 |
| 24(20) | 684.68 | 35.88 | 39.71 | 38.65 | 570.01 | 118.02 | 247.83 ± 297.82 |
| 27(23) | 915.01 | 40.56 | 49.08 | 45.60 | 832.28 | 224.35 | 351.15 ± 411.48 |
| 29(25) | 1072.26 | 62.74 | 58.28 | 49.56 | 1026.44 | 286.98 | 426.04 ± 491.20 |
| 31(27) | 1407.73 | 82.61 | 74.07 | 61.12 | 1275.63 | 374.98 | 546.02 ± 628.77 |
| 34(30) | 1882.88 | 134.86 | 104.57 | 86.54 | 1304.30 | 617.05 | 688.37 ± 751.09 |
| 37(33) | 2264.03 | 205.31 | 140.95 | 117.21 | 1310.60 | 790.98 | 804.85 ± 855.36 |
| 41(37) | 2846.96 | 325.44 | 199.02 | 169.86 | 1408.04 | 1072.15 | 1003.58 ± 1036.21 |
| 44(40) | 3513.39 | 516.59 | 298.55 | 223.82 | 1923.68 | 1703.09 | 1363.19 ± 1280.73 |
| 48(44) | 5715.98 | 743.41 | 422.56 | 260.88 | 2472.54 | 1838.86 | 1909.04 ± 2054.27 |
| 51(47) | euthanized | 1109.63 | 597.90 | 332.20 | 3410.21 | 2491.77 | 1588.34 ± 1315.62 |
| 55(51) | — | 1738.35 | 835.16 | 429.18 | 3994.15 | 3620.28 | 2123.42 ± 1613.89 |
| 58(54) | — | 2321.23 | 1233.71 | 508.69 | 5388.85 | died | 2363.12 ± 2150.29 |

*: Numbers in ( ) are days after received $1^{st}$ treatment

TABLE 11B

Group B (anti-PD1 mAb treatment group) results
Group B: Tumor volume ($mm^3$) in TIGIT&PD1 double gene knock-in mice treated with anti-PD1 mAb (2 mg/kg, n = 6)

| Day(*) | B01 Male | B02 Male | B03 Male | B04 Male | B05 Male | B06 Male | Mean ± SE |
|---|---|---|---|---|---|---|---|
| 5(1)   | 86.80  | 51.12  | 54.93 | 68.40 | 75.25  | 62.81  | 66.55 ± 13.24 |
| 8(4)   | 152.40 | 107.62 | 91.22 | 65.79 | 126.78 | 109.17 | 108.83 ± 29.62 |
| 11(7)  | 48.12  | 35.98  | 40.17 | 27.22 | 66.48  | 50.32  | 44.72 ± 13.56 |
| 15(11) | 35.93  | 25.21  | 56.60 | 55.74 | 30.27  | 33.79  | 39.59 ± 13.35 |
| 17(13) | 0.00   | 14.31  | 0.00  | 0.00  | 15.30  | 0.00   | 4.94 ± 7.65 |
| 21(17) | 0.00   | 0.00   | 0.00  | 0.00  | 0.00   | 0.00   | 0.00 ± 0.00 |
| 24(20) | 0.00   | 0.00   | 0.00  | 0.00  | 0.00   | 0.00   | 0.00 ± 0.00 |
| 27(23) | 0.00   | 0.00   | 0.00  | 0.00  | 0.00   | 0.00   | 0.00 ± 0.00 |
| 29(25) | 0.00   | 0.00   | 0.00  | 0.00  | 0.00   | 0.00   | 0.00 ± 0.00 |
| 31(27) | 0.00   | 0.00   | 0.00  | 0.00  | 0.00   | 0.00   | 0.00 ± 0.00 |
| 34(30) | 0.00   | 0.00   | 0.00  | 0.00  | 0.00   | 0.00   | 0.00 ± 0.00 |
| 37(33) | 0.00   | 0.00   | 0.00  | 0.00  | 0.00   | 0.00   | 0.00 ± 0.00 |
| 41(37) | 0.00   | 0.00   | 0.00  | 0.00  | 0.00   | 0.00   | 0.00 ± 0.00 |
| 44(40) | 0.00   | 0.00   | 0.00  | 0.00  | 0.00   | 0.00   | 0.00 ± 0.00 |
| 48(44) | 0.00   | 0.00   | 0.00  | 0.00  | 0.00   | 0.00   | 0.00 ± 0.00 |
| 51(47) | 0.00   | 0.00   | 0.00  | 0.00  | 0.00   | 0.00   | 0.00 ± 0.00 |
| 55(51) | 0.00   | 0.00   | 0.00  | 0.00  | 0.00   | 0.00   | 0.00 ± 0.00 |
| 58(54) | 0.00   | 0.00   | 0.00  | 0.00  | 0.00   | 0.00   | 0.00 ± 0.00 |
| 62(58) | 0.00   | 0.00   | 0.00  | 0.00  | 0.00   | 0.00   | 0.00 ± 0.00 |
| 69(65) | 0.00   | 0.00   | 0.00  | 0.00  | 0.00   | 0.00   | 0.00 ± 0.00 |
| 73(69) | 0.00   | 0.00   | 0.00  | 0.00  | 0.00   | 0.00   | 0.00 ± 0.00 |
| 76(72) | 0.00   | 0.00   | 0.00  | 0.00  | 0.00   | 0.00   | 0.00 ± 0.00 |

*: Numbers in ( ) are days after received 1st treatment

TABLE 11C

Group C (anti-TIGIT mAb treatment group) results
Group C: Tumor volume ($mm^3$) in TIGIT&PD1 double gene knock-in mice treated with anti-TIGIT mAb (2 mg/kg, n = 6)

| Day(*) | C01 Male | C02 Male | C03 Male | C04 Male | C05 Male | C06 Male | Mean ± SE |
|---|---|---|---|---|---|---|---|
| 5(1)   | 106.79  | 81.42 | 77.65  | 62.77 | 72.23 | 93.36 | 82.37 ± 15.67 |
| 8(4)   | 168.34  | 68.14 | 102.38 | 97.51 | 95.96 | 76.29 | 101.44 ± 35.39 |
| 11(7)  | 128.08  | 43.92 | 51.08  | 61.75 | 47.36 | 33.65 | 60.97 ± 34.13 |
| 15(11) | 94.35   | 35.73 | 56.64  | 32.36 | 44.75 | 28.01 | 48.64 ± 24.60 |
| 17(13) | 110.14  | 10.82 | 23.58  | 0.00  | 0.00  | 0.00  | 24.09 ± 43.18 |
| 21(17) | 123.42  | 0.00  | 6.02   | 0.00  | 0.00  | 0.00  | 21.57 ± 49.95 |
| 24(20) | 119.85  | 0.00  | 6.02   | 0.00  | 0.00  | 0.00  | 20.98 ± 48.50 |
| 27(23) | 194.07  | 0.00  | 0.00   | 0.00  | 0.00  | 0.00  | 0.00 ± 0.00# |
| 29(25) | 267.87  | 0.00  | 0.00   | 0.00  | 0.00  | 0.00  | 0.00 ± 0.00# |
| 31(27) | 394.18  | 0.00  | 0.00   | 0.00  | 0.00  | 0.00  | 0.00 ± 0.00# |
| 34(30) | 572.22  | 0.00  | 0.00   | 0.00  | 0.00  | 0.00  | 0.00 ± 0.00# |
| 37(33) | 773.32  | 0.00  | 0.00   | 0.00  | 0.00  | 0.00  | 0.00 ± 0.00# |
| 41(37) | 1238.33 | 0.00  | 0.00   | 0.00  | 0.00  | 0.00  | 0.00 ± 0.00# |
| 44(40) | 1447.80 | 0.00  | 0.00   | 0.00  | 0.00  | 0.00  | 0.00 ± 0.00# |
| 48(44) | 2075.57 | 0.00  | 0.00   | 0.00  | 0.00  | 0.00  | 0.00 ± 0.00# |
| 51(47) | 2320.37 | 0.00  | 0.00   | 0.00  | 0.00  | 0.00  | 0.00 ± 0.00# |
| 55(51) | 3136.48 | 0.00  | 0.00   | 0.00  | 0.00  | 0.00  | 0.00 ± 0.00# |
| 58(54) | 3786.16 | 0.00  | 0.00   | 0.00  | 0.00  | 0.00  | 0.00 ± 0.00# |
| 62(58) |         | 0.00  | 0.00   | 0.00  | 0.00  | 0.00  | 0.00 ± 0.00# |
| 69(65) |         | 0.00  | 0.00   | 0.00  | 0.00  | 0.00  | 0.00 ± 0.00# |
| 73(69) |         | 0.00  | 0.00   | 0.00  | 0.00  | 0.00  | 0.00 ± 0.00# |
| 76(72) |         | 0.00  | 0.00   | 0.00  | 0.00  | 0.00  | 0.00 ± 0.00# |

*: Numbers in ( ) are days after received 1st treatment
Mean ± SE (without C01 animal, n = 5)

TABLE 11D

Group D (anti-PD1 mAb and anti-TIGIT mAb combination group) results
Group D: Tumor volume ($mm^3$) in TIGIT&PD1 double gene knock-in mice treated with anti-PD1 mAb (1 mg/kg) and anti-TIGIT mAb (1 mg/kg, n = 6)

| Day(*) | D01 Male | D02 Male | D03 Male | D04 Male | D05 Male | D06 Male | Mean ± SE |
|---|---|---|---|---|---|---|---|
| 5(1)   | 97.47  | 69.30  | 79.16 | 44.13 | 85.56 | 100.77 | 79.40 ± 20.82 |
| 8(4)   | 159.66 | 113.86 | 99.46 | 60.35 | 86.32 | 113.44 | 105.52 ± 33.19 |
| 11(7)  | 69.55  | 46.36  | 46.03 | 24.01 | 58.48 | 60.28  | 50.79 ± 15.88 |
| 15(11) | 21.97  | 0.00   | 0.00  | 0.00  | 59.29 | 41.38  | 20.44 ± 25.31 |
| 17(13) | 0.00   | 0.00   | 0.00  | 0.00  | 0.00  | 0.00   | 0.00 ± 0.00 |
| 21(17) | 0.00   | 0.00   | 0.00  | 0.00  | 0.00  | 0.00   | 0.00 ± 0.00 |
| 24(20) | 0.00   | 0.00   | 0.00  | 0.00  | 0.00  | 0.00   | 0.00 ± 0.00 |
| 27(23) | 0.00   | 0.00   | 0.00  | 0.00  | 0.00  | 0.00   | 0.00 ± 0.00 |
| 29(25) | 0.00   | 0.00   | 0.00  | 0.00  | 0.00  | 0.00   | 0.00 ± 0.00 |
| 31(27) | 0.00   | 0.00   | 0.00  | 0.00  | 0.00  | 0.00   | 0.00 ± 0.00 |
| 34(30) | 0.00   | 0.00   | 0.00  | 0.00  | 0.00  | 0.00   | 0.00 ± 0.00 |
| 37(33) | 0.00   | 0.00   | 0.00  | 0.00  | 0.00  | 0.00   | 0.00 ± 0.00 |
| 41(37) | 0.00   | 0.00   | 0.00  | 0.00  | 0.00  | 0.00   | 0.00 ± 0.00 |
| 44(40) | 0.00   | 0.00   | 0.00  | 0.00  | 0.00  | 0.00   | 0.00 ± 0.00 |
| 48(44) | 0.00   | 0.00   | 0.00  | 0.00  | 0.00  | 0.00   | 0.00 ± 0.00 |
| 51(47) | 0.00   | 0.00   | 0.00  | 0.00  | 0.00  | 0.00   | 0.00 ± 0.00 |
| 55(51) | 0.00   | 0.00   | 0.00  | 0.00  | 0.00  | 0.00   | 0.00 ± 0.00 |
| 58(54) | 0.00   | 0.00   | 0.00  | 0.00  | 0.00  | 0.00   | 0.00 ± 0.00 |
| 62(58) | 0.00   | 0.00   | 0.00  | 0.00  | 0.00  | 0.00   | 0.00 ± 0.00 |
| 69(65) | 0.00   | 0.00   | 0.00  | 0.00  | 0.00  | 0.00   | 0.00 ± 0.00 |
| 73(69) | 0.00   | 0.00   | 0.00  | 0.00  | 0.00  | 0.00   | 0.00 ± 0.00# |
| 76(72) | 0.00   | 0.00   | 0.00  | 0.00  | 0.00  | 0.00   | 0.00 ± 0.00# |

*: Numbers in ( ) are days after received 1st treatment

As shown in Tables 11A-11D and FIGS. 11A-11D, tumor growth was rapid in the 0.9% NaCl vehicle control group (Group A), and no tumor regressed or complete rejection (CR: 0/6) was observed in this test-group animals; whereas in the PD-mAb treatment group (Group B), TIGIT-mAb treatment group (Group C), or PD-1 mAb and TIGIT-mab combination group (Group D), tumor growth was inhibited and tumor regressed or completely disappeared 5-8 days after the treatment.

The results of PD-1 mAb treatment group was in line with what was expected, with a complete rejection (complete rejection: 6/6) or regress of all tumors in all test animals after 2-3 doses (11-13 days after a first dose), and no tumor recurrence was observed during the whole experiment period even after the treatment was stopped (the longest observation was made on the 76th day after tumor inoculation); what is more surprising and encouraging is that in the TIGIT mAb treatment group, except one mouse (animal No. C01) whose tumor growth was not inhibited, all the other 5 mice showed a complete rejection or regression (complete rejection: 5/6), after only 2-3 times of administration (i.e. 11-13 days after a first dose), and no tumor recurrence was observed during the whole experiment period after the treatment was stopped (the longest observation was made on the 76th day after tumor inoculation). In PD-1 mAb and TIGIT mAb combination treatment group, when the individual antibody dose was reduced by half (1 mg/kg), all the tumors in all test animals were regressed or completely rejected (complete rejection: 6/6) after only 2-3 times of treatments (i.e. 11-13 days after the first dose), and no tumor recurrence was observed during the whole experiment period after the treatment was stopped (the longest observation was made on the 76th day after tumor inoculation).

FIG. 12A shows the average tumor growth volume trend in the experimental animals.

FIG. 12B shows the average weight growth trend in the experimental animals.

As shown in FIG. 12B, compared with that in the control group, in the TIGIT mAb treatment group, either administration alone or in combination with PD-mAb, there is no any significant effect on the body weight gain in the tested animals during the experiment.

What is claimed is:

1. A monoclonal antibody or a derivative thereof binding to a TIGIT antigen, comprising a first variable region and a second variable region,
   wherein the first variable region is an antibody light chain variable region comprising complementarity-determining regions CDR1, CDR2, and CDR3 having amino acid sequences as set forth in SEQ ID NO: 9, SEQ ID NO: 10, and SEQ ID NO: 11, respectively; and
   wherein the second variable region is an antibody heavy chain variable region comprising complementarity-determining regions CDR1, CDR2, and CDR3 having amino acid sequences as set forth in SEQ ID NO: 14, SEQ ID NO: 15, and SEQ ID NO: 16, respectively.

2. The monoclonal antibody or the derivative thereof according to claim 1, wherein the monoclonal antibody or the derivative thereof has one or more of the following characteristics:
   a) comprising the antibody light chain variable region and the antibody heavy chain variable region, an amino acid sequence of the antibody light chain variable region is at least 90% identical to an amino acid sequence shown in SEQ ID NO: 17; and an amino acid sequence of the antibody heavy chain variable region is at least 90% identical to an amino acid sequence shown in SEQ ID NO: 19;
   b) a constant value of a binding affinity with a human TIGIT antigen is equal to or less than 10 nM;
   c) antagonistically inhibiting a binding of the TIGIT antigen to its ligand, CD155 (PVR).

3. The monoclonal antibody or the derivative thereof according to claim 2, wherein an $IC_{50}$ value of antagonistically inhibiting the binding of the TIGIT antigen to its ligand CD155 (PVR) is equal to or less than 1 nM.

4. The monoclonal antibody or the derivative thereof according to claim 2, wherein the first variable region is an antibody light chain variable region having the amino acid sequence as set forth in SEQ ID NO: 17; and the second variable region is an antibody heavy chain variable region having the amino acid sequence as set forth in SEQ ID NO: 19.

5. The monoclonal antibody or the derivative thereof according to claim 1, wherein the first variable region is an antibody light chain variable region having an amino acid sequence as set forth in SEQ ID NO: 8; and the second variable region is an antibody heavy chain variable region having an amino acid sequence as set forth in SEQ ID NO: 13.

6. The monoclonal antibody or the derivative thereof according to claim 1, antagonistically inhibiting a binding of the TIGIT antigen to its ligand, CD155 (PVR).

7. The monoclonal antibody or the derivative thereof according to claim 1, comprising the antibody light chain variable region, a human antibody light chain constant region, the antibody heavy chain variable region, and a hinge region of a human antibody heavy chain constant region, a CH1 region, a CH2 region, and a CH3 region.

8. The monoclonal antibody or the derivative thereof according to claim 7, wherein the human antibody light chain constant region is a kappa chain or a lambda chain of a human antibody, the human antibody heavy chain constant region is a human IgG1, IgG2, IgG3, or IgG4 isotype.

9. A DNA molecule or a gene sequence coding the monoclonal antibody or the derivative thereof according to claim 4, wherein a nucleotide sequence coding the antibody light chain variable region is as set forth in SEQ ID NO: 18, and a nucleotide sequence coding the antibody heavy chain variable region is as set forth in SEQ ID NO: 20.

10. A DNA molecule or a gene sequence coding the monoclonal antibody or the derivative thereof according to claim 5, wherein a nucleotide sequence coding the antibody light chain variable region is as set forth in SEQ ID NO: 7, and a nucleotide sequence coding the antibody heavy chain variable region is as set forth in SEQ ID NO: 12.

11. An expression vector comprising a DNA molecule or a gene sequence coding the monoclonal antibody or the derivative thereof according to claim 1 and an expression regulatory sequence operably linked to the DNA molecule or the gene sequence.

12. The expression vector according to claim 11,
wherein the first variable region is an antibody light chain variable region having an amino acid sequence as set forth in SEQ ID NO: 8; and the second variable region is an antibody heavy chain variable region having an amino acid sequence as set forth in SEQ ID NO: 13;
wherein a nucleotide sequence coding the antibody light chain variable region is as set forth in SEQ ID NO: 7, and a nucleotide sequence coding the antibody heavy chain variable region is as set forth in SEQ ID NO: 12.

13. A recombinant host cell transfected with the expression vector according to claim 11.

14. The recombinant host cell according to claim 13, wherein the recombinant host cell expresses the monoclonal antibody or the derivative thereof.

15. A pharmaceutical compound or a pharmaceutical composition, comprising a pharmaceutically valid amount of the monoclonal antibody or the derivative thereof according to claim 1, and a pharmaceutically accepted carrier.

16. The pharmaceutical composition according to claim 15, wherein the pharmaceutical composition further comprises anti-PD-1 antibodies or anti-PDL-1 antibodies.

17. A method of preparing a medicament for a treatment of tumors comprising a step of combining the monoclonal antibody or the derivative thereof according to claim 1 with a pharmaceutically acceptable carrier for the treatment of tumors.

18. A method for preparing the monoclonal antibody or the derivative thereof according to claim 1, wherein the method comprises the following steps:
a) providing an expression vector, wherein the expression vector comprises a DNA molecule or a gene sequence coding the monoclonal antibody or the derivative thereof and an expression regulatory sequence operably linked to the DNA molecule or the gene sequence;
b) transfecting a host cell with the expression vector of step a);
c) culturing the host cell from step b) under conditions suitable for an expression of the monoclonal antibody; and
d) isolating, purifying, and collecting the monoclonal antibody or the derivative from a host cell culture medium by affinity chromatography.

19. The monoclonal antibody or the derivative thereof according to claim 2, antagonistically inhibiting a binding of the TIGIT antigen to its ligand, CD155 (PVR).

20. The monoclonal antibody or the derivative thereof according to claim 3, antagonistically inhibiting a binding of the TIGIT antigen to its ligand, CD155 (PVR).

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: the sequence is synthetized.

<400> SEQUENCE: 1
tgtcgttcac tgccatcaat                                                   20

<210> SEQ ID NO 2
<211> LENGTH: 21
<212> TYPE: DNA
<213> ORGANISM: Artificial Sequence
<220> FEATURE:
<223> OTHER INFORMATION: the sequence is synthetized.

<400> SEQUENCE: 2
gcaaggctta caaccacaat c                                                 21

<210> SEQ ID NO 3
<211> LENGTH: 13
<212> TYPE: DNA
<213> ORGANISM: Artificial Sequence
<220> FEATURE:
<223> OTHER INFORMATION: the sequence is synthetized.

<400> SEQUENCE: 3
gacatccaga tga                                                          13

<210> SEQ ID NO 4
<211> LENGTH: 20
<212> TYPE: DNA
<213> ORGANISM: Artificial Sequence
<220> FEATURE:
<223> OTHER INFORMATION: the sequence is synthetized.

<400> SEQUENCE: 4
ctgaggcacc tccagatgtt                                                   20

<210> SEQ ID NO 5
<211> LENGTH: 17
<212> TYPE: DNA
<213> ORGANISM: Artificial Sequence
<220> FEATURE:
<223> OTHER INFORMATION: the sequence is synthetized.

<400> SEQUENCE: 5
gtgcagtctg gacctga                                                      17

<210> SEQ ID NO 6
<211> LENGTH: 21
<212> TYPE: DNA
<213> ORGANISM: Artificial Sequence
<220> FEATURE:
<223> OTHER INFORMATION: the sequence is synthetized.
```

<400> SEQUENCE: 6
gtgctggagg ggacagtcac t                                          21

<210> SEQ ID NO 7
<211> LENGTH: 321
<212> TYPE: DNA
<213> ORGANISM: Mus musculus

<400> SEQUENCE: 7
gacattgtga tgacccagtc tcacaaattc atgtccacat cattaggaga cagggtcagc      60
atcacctgca aggccagtca ggatgtgggt tctactgtag cctggtatca acagaaacca     120
gggcaatctc ctaaactact gatttactgg gcatccaccc gccacactgg agtccctgat     180
cgcttcacag gcagtggatc tgggacagat ttcactctca ccattaccaa tgtgcagtct     240
gaagacttgg cagattattt ctgtcagcaa tataccagct ttccgtacac gttcggaggg     300
gggaccaagc tggaaataaa a                                              321

<210> SEQ ID NO 8
<211> LENGTH: 107
<212> TYPE: PRT
<213> ORGANISM: Mus musculus

<400> SEQUENCE: 8

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ser Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Thr Ser Phe Pro Tyr
                85                  90                  95

Thr Phe Gly Gly Gly Thr Lys Leu Glu Ile Lys
            100                 105

<210> SEQ ID NO 9
<211> LENGTH: 11
<212> TYPE: PRT
<213> ORGANISM: Mus musculus

<400> SEQUENCE: 9

Lys Ala Ser Gln Asp Val Gly Ser Thr Val Ala
1               5                   10

<210> SEQ ID NO 10
<211> LENGTH: 7
<212> TYPE: PRT
<213> ORGANISM: Mus musculus

<400> SEQUENCE: 10

Trp Ala Ser Thr Arg His Thr
1               5

<210> SEQ ID NO 11
<211> LENGTH: 9

<210> SEQ ID NO 11
<211> LENGTH: 9
<212> TYPE: PRT
<213> ORGANISM: Mus musculus

<400> SEQUENCE: 11

Gln Gln Tyr Thr Ser Phe Pro Tyr Thr
1               5

<210> SEQ ID NO 12
<211> LENGTH: 357
<212> TYPE: DNA
<213> ORGANISM: Mus musculus

<400> SEQUENCE: 12
gaggtccagc tgcagcagtc tggacctgac ctggtgaagc ctggggcttc agtgaagata    60
tcctgcaagg cttctggtta ctcattcact ggctactaca tgcactgggt gaagcagagc   120
catggaaaga gccttgagtg gattggacgt gttaatccta acaatggtga tactcgctac   180
aaccagaagt tcaagggcaa ggccatatta actgtagaca agtcatccag cacagcctac   240
atggagctcc gcagcctgac atctgaggac tctgcggtct attactgtgc aagagaggga   300
gattacgacg agaggtttgc ttactggggc caagggactc tggtcactgt ctctgca      357

<210> SEQ ID NO 13
<211> LENGTH: 119
<212> TYPE: PRT
<213> ORGANISM: Mus musculus

<400> SEQUENCE: 13

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Val Asn Pro Asn Asn Gly Asp Thr Arg Tyr Asn Gln Lys Phe
    50                  55                  60

Lys Gly Lys Ala Ile Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Glu Gly Asp Tyr Asp Glu Arg Phe Ala Tyr Trp Gly Gln Gly
            100                 105                 110

Thr Leu Val Thr Val Ser Ala
        115

<210> SEQ ID NO 14
<211> LENGTH: 5
<212> TYPE: PRT
<213> ORGANISM: Mus musculus

<400> SEQUENCE: 14

Gly Tyr Tyr Met His
1               5

<210> SEQ ID NO 15
<211> LENGTH: 17
<212> TYPE: PRT
<213> ORGANISM: Mus musculus

<400> SEQUENCE: 15

Arg Val Asn Pro Asn Asn Gly Asp Thr Arg Tyr Asn Gln Lys Phe Lys
1               5                   10                  15
Gly

<210> SEQ ID NO 16
<211> LENGTH: 12
<212> TYPE: PRT
<213> ORGANISM: Mus musculus

<400> SEQUENCE: 16

Ala Arg Glu Gly Asp Tyr Asp Glu Arg Phe Ala Tyr
1               5                   10

<210> SEQ ID NO 17
<211> LENGTH: 107
<212> TYPE: PRT
<213> ORGANISM: Homo sapiens

<400> SEQUENCE: 17

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Ser Thr
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Thr Ser Phe Pro Tyr
                85                  90                  95

Thr Phe Gly Gly Gly Thr Lys Leu Glu Ile Lys
            100                 105

<210> SEQ ID NO 18
<211> LENGTH: 321
<212> TYPE: DNA
<213> ORGANISM: Homo sapiens

<400> SEQUENCE: 18
gacatccagc tgacccagtc cccctccttt ctgtccgcct ccgtgggcga cagggtgacc     60
atcacctgca aggcctccca ggacgtgggc tccacagtgg cctggtacca gcagaagccc    120
ggcaaggccc ccaagctgct gatctactgg gcttccacca ggcacaccgg cgtgccttcc    180
aggttctccg gatccggctc cggcaccgag ttcaccctga ccatctcctc cctgcagccc    240
gaggacttcg ccacctacta ctgccagcag tacacctcct tcccctacac cttcggcggc    300
ggcaccaagc tggagatcaa g                                              321

<210> SEQ ID NO 19
<211> LENGTH: 119
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

```
Tyr Met His Trp Val Arg Gln Ala Pro Gly Gln Gly Leu Glu Trp Met
        35                  40                  45
Gly Arg Val Asn Pro Asn Asn Gly Asp Thr Arg Tyr Asn Gln Lys Phe
 50                  55                  60
Lys Gly Arg Val Thr Met Thr Arg Asp Thr Ser Ile Ser Thr Ala Tyr
 65                  70                  75                  80
Met Glu Leu Ser Arg Leu Arg Ser Asp Thr Val Val Tyr Tyr Cys
                 85                  90                  95
Ala Arg Glu Gly Asp Tyr Asp Glu Arg Phe Ala Tyr Trp Gly Gln Gly
                100                 105                 110
Thr Leu Val Thr Val Ser Ala
        115

<210> SEQ ID NO 20
<211> LENGTH: 357
<212> TYPE: DNA
<213> ORGANISM: Homo sapiens

<400> SEQUENCE: 20
caggtgcagc tggtgcagtc cggcgctgag gtgaagaagc ccggagcctc cgtgaaggtg      60
tcctgcaagg cctccggcta ctccttcacc ggctactaca tgcactgggt gaggcaagcc     120
cctggacagg gcctggagtg gatgggcagg gtgaaccca acaacggcga caccaggtac      180
aaccagaagt tcaagggccg ggtgaccatg accagggaca cctccatctc caccgcctac    240
atggagctgt ccaggctgag gtccgacgac accgtggtgt actactgcgc cagggagggc    300
gactacgacg agaggttcgc ctactggggc cagggaaccc tggtgaccgt gagcgcc       357
```